(12) United States Patent
Martin et al.

(10) Patent No.: US 7,531,319 B2
(45) Date of Patent: May 12, 2009

(54) ARRAY FOR RAPID DETECTION OF A MICROORGANISM

(75) Inventors: Stephanie M. Martin, Woodstock, GA (US); J. Gavin MacDonald, Decatur, GA (US); Jason Lye, Atlanta, GA (US); Curtis Sayre, Atlanta, GA (US); Kimberlee Thompson, Chattanooga, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 330 days.

(21) Appl. No.: 11/513,501

(22) Filed: Aug. 31, 2006

(65) Prior Publication Data

US 2008/0057533 A1 Mar. 6, 2008

(51) Int. Cl.
*C12P 1/00* (2006.01)
(52) U.S. Cl. .......................................... 435/41
(58) Field of Classification Search .................. None
See application file for complete search history.

(56) References Cited

U.S. PATENT DOCUMENTS

| | | | |
|---|---|---|---|
| 3,338,992 A | 8/1967 | Kinney |
| 3,341,394 A | 9/1967 | Kinney |
| 3,368,549 A | 2/1968 | Barr et al. |
| 3,494,821 A | 2/1970 | Evans |
| 3,502,538 A | 3/1970 | Peterson |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,918,433 A | 11/1975 | Fuisz |
| 4,100,324 A | 7/1978 | Anderson et al. |
| 4,144,370 A | 3/1979 | Boulton |
| 4,340,563 A | 7/1982 | Appel et al. |
| 4,556,636 A | 12/1985 | Belly et al. |
| 4,578,359 A | 3/1986 | Oksman et al. |
| 5,057,361 A | 10/1991 | Sayovitz et al. |
| 5,181,905 A | 1/1993 | Flam |
| 5,217,444 A | 6/1993 | Schoenfeld |
| 5,284,703 A | 2/1994 | Everhart et al. |
| 5,350,624 A | 9/1994 | Georger et al. |
| 5,382,400 A | 1/1995 | Pike et al. |
| 5,449,612 A | 9/1995 | Lepargneur et al. |
| 5,468,236 A | 11/1995 | Everhart et al. |
| 5,540,332 A | 7/1996 | Kopacz et al. |
| 5,667,635 A | 9/1997 | Win et al. |
| 5,681,380 A | 10/1997 | Nohr et al. |
| 5,744,321 A | 4/1998 | Harewood |
| 5,785,179 A | 7/1998 | Buczwinski et al. |
| 5,888,524 A | 3/1999 | Cole |
| 5,910,421 A | 6/1999 | Small, Jr. et al. |
| 5,964,351 A | 10/1999 | Zander |
| 6,028,018 A | 2/2000 | Amundson et al. |
| 6,030,331 A | 2/2000 | Zander |
| 6,060,256 A | 5/2000 | Everhart et al. |
| 6,090,541 A | 7/2000 | Wicks et al. |
| 6,158,614 A | 12/2000 | Haines et al. |
| 6,197,574 B1 | 3/2001 | Miyamoto et al. |
| 6,207,596 B1 | 3/2001 | Rourke et al. |
| 6,269,969 B1 | 8/2001 | Huang et al. |
| 6,269,970 B1 | 8/2001 | Huang et al. |
| 6,273,359 B1 | 8/2001 | Newman et al. |
| 6,315,864 B2 | 11/2001 | Anderson et al. |
| 6,368,558 B1 | 4/2002 | Suslick et al. |
| 6,387,651 B1 | 5/2002 | Bochner et al. |
| 6,433,244 B1 | 8/2002 | Roe et al. |
| 6,436,651 B1 | 8/2002 | Everhart et al. |
| 6,440,437 B1 | 8/2002 | Krzysik et al. |
| 6,479,727 B1 | 11/2002 | Roe |
| 6,501,002 B1 | 12/2002 | Roe et al. |
| 6,542,379 B1 | 4/2003 | Lauffer et al. |
| 6,551,791 B1 | 4/2003 | Small et al. |

(Continued)

FOREIGN PATENT DOCUMENTS

| | | |
|---|---|---|
| EP | 1143246 A1 | 10/2001 |
| EP | 1527888 A2 | 5/2005 |
| GB | 2178847 | 2/1987 |
| JP | 2005253412 A | 9/2005 |
| WO | WO 8905093 | 6/1989 |

(Continued)

OTHER PUBLICATIONS

Bochner et al. "Phenotype microarrays for high-throughput phenotypic testing and assay of gene function", Genome Research, 2001, 11:1246-1255.*
Search Report and Written Opinion for PCT/IB2007/052871, Feb. 27, 2008.
*Color and Constitution of Organic Molecules*—Academic Press, (1976) p. 11.

(Continued)

*Primary Examiner*—Jon P Weber
*Assistant Examiner*—Bin Shen
(74) *Attorney, Agent, or Firm*—Dority & Manning, P.A.

(57) ABSTRACT

A method for detecting a microorganism or class of microorganisms is provided. More specifically, the method employs an array that contains a plurality of discrete regions (referred to as "addresses") spaced apart on a solid support in a predetermined pattern. The addresses are selected so that the array provides a distinct spectral response (e.g., pattern of colors) or "fingerprint" for a particular microorganism or class of microorganisms. For example, the array may provide a certain spectral response in the presence of one microorganism or class of microorganisms (e.g., gram-negative bacteria), but provide a completely different spectral response in the presence of another microorganism or class of microorganisms (e.g., gram-positive bacteria). Detection of the spectral response provided by the array may thus allow for differentiation between microorganisms.

26 Claims, 1 Drawing Sheet

U.S. PATENT DOCUMENTS

| | | |
|---|---|---|
| 6,589,761 B1 | 7/2003 | Freadman et al. |
| 6,645,930 B1 | 11/2003 | Wallis et al. |
| 6,713,660 B1 | 3/2004 | Roe et al. |
| 6,951,730 B2 | 10/2005 | Small et al. |
| 6,967,084 B2 | 11/2005 | Small et al. |
| 2002/0177828 A1 | 11/2002 | Batich et al. |
| 2003/0119202 A1 | 6/2003 | Kaylor et al. |
| 2003/0143112 A1 | 7/2003 | Suslick et al. |
| 2004/0014161 A1 | 1/2004 | Janes et al. |
| 2004/0029171 A1 | 2/2004 | Wagner et al. |
| 2004/0113801 A1 | 6/2004 | Gustafson et al. |
| 2004/0172000 A1 | 9/2004 | Roe et al. |
| 2005/0084464 A1 | 4/2005 | McGrath et al. |
| 2005/0101841 A9 | 5/2005 | Kaylor et al. |
| 2005/0112085 A1 | 6/2005 | MacDonald et al. |
| 2005/0124072 A1 | 6/2005 | Boga et al. |
| 2005/0130253 A1 | 6/2005 | Lye et al. |
| 2005/0136238 A1 | 6/2005 | Lindsay et al. |
| 2005/0160543 A1 | 7/2005 | Catalfamo et al. |
| 2005/0250089 A1 | 11/2005 | Chandrapati et al. |
| 2005/0250168 A1 | 11/2005 | Gonzalez et al. |
| 2005/0250169 A1 | 11/2005 | Gonzalez et al. |
| 2006/0000043 A1 | 1/2006 | Jou-Chen et al. |
| 2006/0003649 A1 | 1/2006 | Runge et al. |
| 2006/0062689 A1 | 3/2006 | Kirollos et al. |
| 2006/0114754 A1 | 6/2006 | MacDonald et al. |
| 2006/0134613 A1 | 6/2006 | Martin et al. |
| 2006/0134728 A1 | 6/2006 | MacDonald et al. |
| 2006/0210970 A1 | 9/2006 | Debad et al. |

FOREIGN PATENT DOCUMENTS

| | | |
|---|---|---|
| WO | WO 0055359 A1 | 9/2000 |
| WO | WO 0171318 A1 | 9/2001 |
| WO | WO 0185081 A1 | 11/2001 |
| WO | WO 0230478 A2 | 4/2002 |
| WO | WO 0230478 A3 | 4/2002 |
| WO | WO 2005042771 A2 | 5/2005 |
| WO | WO 2005059162 A2 | 6/2005 |
| WO | WO 2006105193 A2 | 10/2006 |
| WO | WO 2006105193 A3 | 10/2006 |
| WO | WO 2007009047 A2 | 1/2007 |
| WO | WO 2007027899 A1 | 3/2007 |

OTHER PUBLICATIONS

Koidl et al.—*Rapid Diagnosis of Adenoviral Keratoconjunctivitis by a Fully Automated Molecular Assay*, Ophtalmology, vol. 112, No. 9 Sep. 2005, pp. 1521.e1-1521.e8.

U.S. Appl. No. 11/513,500, filed Aug. 31, 2006, Martin et al. Method for Detecting *Candida* on Skin.

* cited by examiner

ARRAY FOR RAPID DETECTION OF A MICROORGANISM

BACKGROUND OF THE INVENTION

The ability to rapidly detect microorganisms is becoming an increasing problem in a wide variety of industries, includes the medical and food industries. For instance, rapid detection of a microorganism in the medical field may be crucial for proper diagnosis and treatment of an illness. Unfortunately, multiple etiologic agents may be responsible for a particular condition, thereby making it difficult to rapidly identify the cause of the condition. The need for selective identification of the type of microorganism is important for a variety of reasons. For example, the knowledge of which type of microorganism is present may lead one to identify the particular source of contamination and to choose an appropriate treatment. Most of the current diagnostic procedures involve culturing the microorganism for identification, a process that usually requires several days and often gives negative results. Not only is culturing a lengthy process, but certain pathogens (e.g., mycobacteria) are notoriously difficult to grow outside the host. Although "non-culturing" techniques have been developed, they are typically designed for only a specific pathogen. Thus, several assays are required to obtain a diagnosis, which are expensive and time-consuming.

As such, a need currently exists for a technique of rapidly and simply detecting the presence of microorganisms, and identifying the particular type of detected microorganism.

SUMMARY OF THE INVENTION

In accordance with one embodiment of the present invention, a method for detecting a microorganism in a sample is disclosed. The method comprises contacting the sample with an array, the array comprising a plurality of individual array addresses spaced apart in a predetermined pattern on a solid support. The addresses each contain a colorant so that the array produces a visually observable spectral response. The spectral response is detected (e.g., visually) and correlated to the presence of one or more microorganisms.

In accordance with another embodiment of the present invention, an array for detecting a microorganism in a sample is disclosed. The array comprises a plurality of individual array addresses spaced apart in a predetermined pattern on a solid support. The addresses each contain a colorant so that the array produces a visually observable spectral response that is distinct for one or more microorganisms.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1A:
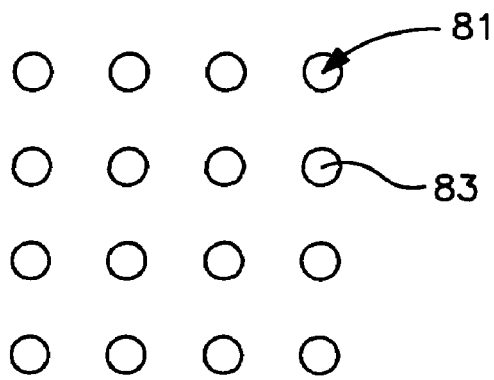
FIG. 1 is a perspective view of an exemplary array of the present invention prior to contact with a test sample (FIG. 1A), after contact with a test sample infected with E. coli (FIG. 1B); and after contact with a test sample infected with S. aureus (FIG. 1C).

Repeat use of reference characters in the present specification and drawing is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a method for detecting a microorganism or class of microorganisms. More specifically, the method employs an array that contains a plurality of discrete regions (referred to as "addresses") spaced apart on a solid support in a predetermined pattern. The addresses are selected so that the array provides a distinct spectral response (e.g., pattern of colors) or "fingerprint" for a particular microorganism or class of microorganisms. For example, the array may provide a certain spectral response in the presence of one microorganism or class of microorganisms (e.g., gram-negative bacteria), but provide a completely different spectral response in the presence of another microorganism or class of microorganisms (e.g., gram-positive bacteria). Detection of the spectral response provided by the array may thus allow for differentiation between microorganisms.

The array addresses contain a colorant capable of exhibiting a color change in the presence of one or more microorganisms. That is, the colorant may change from a first color to a second color, from colorless to a color, or from a color to colorless. A variety of colorants (e.g., dyes, pigments, etc.) may be employed in the array of the present invention. In one embodiment, for example, pH-sensitive colorants are employed that are capable of differentiating between certain types of microorganisms. Namely, pH-sensitive colorants can detect a change in the pH of the growth medium of the microorganism. Bacteria, for instance, may metabolize the growth medium and generate acidic compounds (e.g., $CO_2$) or basic compounds (e.g., ammonia) that lead to a change in pH. Likewise, certain microorganisms (e.g., bacteria) contain highly organized acid moieties on their cell walls. Because the acidic/basic shift may vary for different microorganisms, pH-sensitive colorants may be selected in the present invention that are tuned for the desired pH transition. In this manner, array addresses may be provided with pH-sensitive colorants that are configured to undergo a detectable color change only in the presence of microorganisms exhibiting a certain acidic/basic shift.

Phthalein colorants constitute one class of suitable pH-sensitive colorants that may be employed in the array of the present invention. Phenol Red (i.e., phenolsulfonephthalein), for example, exhibits a transition from yellow to red over the pH range 6.6 to 8.0. Above a pH of about 8.1, Phenol Red turns a bright pink (fuschia) color. Derivatives of Phenol Red may also be suitable for use in the present invention, such as those substituted with chloro, bromo, methyl, sodium carboxylate, carboxylic acid, hydroxyl and amine functional groups. Exemplary substituted Phenol Red compounds include, for instance, Chlorophenol Red, Metacresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',3",5',5"-tetrabromophenolsulfonephthalein), Bromochlorophenol Blue (the sodium salt of dibromo-5',5"-dichlorophenolsulfonephthalein), Bromocresol Purple (5',5"-dibromo-ortho-cresolsulfonephthalein), Bromocresol Green (3',3",5',5"-tetrabromo-ortho-cresolsulfonephthalein), and so forth. Still other suitable phthalein colorants are well known in the art, and may include Bromothymol Blue, Thymol Blue, Bromocresol Purple, thymolphthalein, and phenolphthalein (a common component of universal indicators). For example, Chlorophenol Red exhibits a transition from yellow to red over a pH range of about 4.8 to 6.4; Bromothymol Blue exhibits a transition from yellow to blue over a pH range of about 6.0 to 7.6; thymolphthalein exhibits a transition from colorless to blue over a pH range of about 9.4 to 10.6; phenolphthalein exhibits a transition from colorless to pink over a pH range of about 8.2 to 10.0; Thymol Blue exhibits a first transition from red to yellow over a pH range of about 1.2 to 2.8 and a second transition from yellow to pH over a pH range of 8.0 to 9.6; Bromophenol Blue exhibits a transition from yellow to violet over a pH range of about 3.0 to 4.6; Bromocresol Green exhibits a transition from yellow to blue over a pH range of about 3.8 to 5.4; and Bromocresol Purple exhibits a transition from yellow to violet over a pH of about 5.2 to 6.8.

Hydroxyanthraquinones constitute another suitable class of pH-sensitive colorants for use in the present invention. Hydroxyanthraquinones have the following general structure:

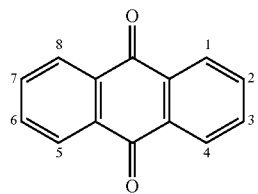

The numbers 1-8 shown in the general formula represent a location on the fused ring structure at which substitution of a functional group may occur. For hydroxyanthraquinones, at least one of the functional groups is or contains a hydroxy (—OH) group. Other examples of functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, phosphorous groups, etc. Some suitable hydroxyanthraquinones that may be used in the present invention, Mordant Red 11 (Alizarin), Mordant Red 3 (Alizarin Red S), Alizarin Yellow R, Alizarin Complexone, Mordant Black 13 (Alizarin Blue Black B), Mordant Violet 5 (Alizarin Violet 3R), Alizarin Yellow GG, Natural Red 4 (carminic acid), amino-4-hydroxyanthraquinone, Emodin, Nuclear Fast Red, Natural Red 16 (Purpurin), Quinalizarin, and so forth. For instance, carminic acid exhibits a first transition from orange to red over a pH range of about 3.0 to 5.5 and a second transition from red to purple over a pH range of about 5.5 to 7.0. Alizarin Yellow R, on the other hand, exhibits a transition from yellow to orange-red over a pH range of about 10.1 to 12.0.

Yet another suitable class of pH-sensitive colorants that may be employed in the array is aromatic azo compounds having the general structure:

$$X—R_1—N=N—R_2—Y$$

wherein, $R_1$ is an aromatic group;

$R_2$ is selected from the group consisting of aliphatic and aromatic groups; and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, halides, etc. Also suitable are azo derivatives, such as azoxy compounds (X—$R_1$—N=NO—$R_2$—Y) or hydrazo compounds (X—$R_1$—NH—NH—$R_2$—Y). Particular examples of such azo compounds (or derivatives thereof) include Methyl Violet, Methyl Yellow, Methyl Orange, Methyl Red, and Methyl Green. For instance, Methyl Violet undergoes a transition from yellow to blue-violet at a pH range of about 0 to 1.6, Methyl Yellow undergoes a transition from red to yellow at a pH range of about 2.9 to 4.0, Methyl Orange undergoes a transition from red to yellow at a pH range of about 3.1 to 4.4, and Methyl Red undergoes a transition from red to yellow at a pH range of about 4.2 to 6.3.

Arylmethanes (e.g., diarylmethanes and triarylmethanes) constitute still another class of suitable pH-sensitive colorants for use in the present invention. Triarylmethane leuco bases, for example, have the following general structure:

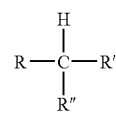

wherein R, R', and R" are independently selected from substituted and unsubstituted aryl groups, such as phenyl, naphthyl, anthracenyl, etc. The aryl groups may be substituted with functional groups, such as amino, hydroxyl, carbonyl, carboxyl, sulfonic, alkyl, and/or other known functional groups. Examples of such triarylmethane leuco bases include Leucomalachite Green, Pararosaniline Base, Crystal Violet Lactone, Crystal Violet Leuco, Crystal Violet, Cl Basic Violet 1, Cl Basic Violet 2, Cl Basic Blue, Cl Victoria Blue, N-benzoyl leuco-methylene, etc. Likewise suitable diarylmethane leuco bases may include 4,4'-bis (dimethylamino) benzhydrol (also known as "Michler's hydrol"), Michler's hydrol leucobenzotriazole, Michler's hydrol leucomorpholine, Michler's hydrol leucobenzenesulfonamide, etc. In one particular embodiment, the colorant is Leucomalachite Green Carbinol (Solvent Green 1) or an analog thereof, which is normally colorless and has the following structure:

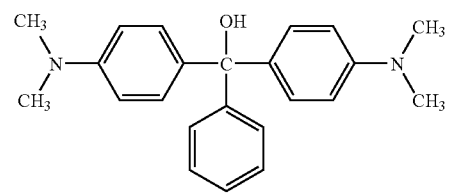

Under acidic conditions, one or more free amino groups of the Leucomalachite Green Carbinol form may be protonated to form Malachite Green (also known as Aniline Green, Basic Green 4, Diamond Green B, or Victoria Green B), which has the following structure:

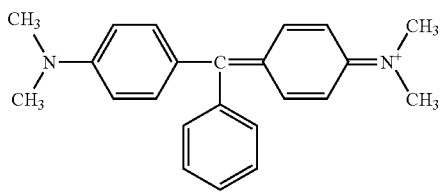

Malachite Green typically exhibits a transition from yellow to blue-green over a pH range 0.2 to 1.8. Above a pH of about 1.8, malachite green turns a deep green color.

Still other suitable pH-sensitive colorants that may be employed in the array include Congo Red, Litmus (azolitmin), Methylene Blue, Neutral Red, Acid Fuchsin, Indigo Carmine, Brilliant Green, Picric acid, Metanil Yellow, m-Cresol Purple, Quinaldine Red, Tropaeolin OO, 2,6-dinitrophenol, Phloxine B, 2,4-dinitrophenol, 4-dimethylaminoazobenzene, 2,5-dinitrophenol, 1-Naphthyl Red, Chlorophenol Red, Hematoxylin, 4-nitrophenol, nitrazine yellow, 3-nitrophenol, Alkali Blue, Epsilon Blue, Nile Blue A, universal indicators, and so forth. For instance, Congo Red undergoes a transition from blue to red at a pH range of about 3.0 to 5.2, Litmus undergoes a transition from red to blue at a pH range of about 4.5 to 8.3, and Neutral Red undergoes a transition from red to yellow at a pH range of about 11.4 to 13.0.

In addition to pH, other mechanisms may also be wholly or partially responsible for inducing a color change in the colorant. For example, many microorganisms (e.g., bacteria and fungi) produce low molecular weight iron-complexing compounds in growth media, which are known as "siderophores." Metal complexing colorants may thus be employed in some embodiments of the present invention that undergo a color change in the presence of siderophores. One particularly suitable class of metal complexing colorants are aromatic azo compounds, such as Eriochrome Black T, Eriochrome Blue SE, Eriochrome Blue Black B, Eriochrome Cyanine R, Xylenol Orange, Chrome Azurol S, carminic acid, etc. Still other suitable metal complexing colorants may include Alizarin Complexone, Alizarin S, Arsenazo III, Aurintricarboxylic acid, 2,2'-Bipyidine, Bromopyrogallol Red, Calcon (Eriochrome Blue Black R), Calconcarboxylic acid, Chromotropic acid, disodium salt, Cuprizone, 5-(4-Dimethylamino-benzylidene)rhodanine, Dimethylglyoxime, 1,5-Diphenylcarbazide, Dithizone, Fluorescein Complexone, Hematoxylin, 8-Hydroxyquinoline, 2-Mercaptobenzothiazole, Methylthymol Blue, Murexide, 1-Nitroso-2-naphthol, 2-Nitroso-1-naphthol, Nitroso-R-salt, 1,10-Phenanthroline, Phenylfluorone, Phthalein Purple, 1-(2-Pyridylazo)-naphthol, 4-(2-Pyridylazo)resorcinol, Pyrogallol Red, Sulfonazo III, 5-Sulfosalicylic acid, 4-(2-Thiazolylazo)resorcinol, Thorin, Thymolthalexon, Tiron, Tolurnr-3,4-dithiol, Zincon, and so forth. It should be noted that one or more of the pH-sensitive colorants referenced above may also be classified as metal complexing colorants.

Of course, the colorants need not be capable of independently differentiating between particular microorganisms, so long as the overall spectral response provided by the array is distinct. In this regard, colorants may also be employed that exhibit a detectable color change in the presence of a broad spectrum of microorganisms. Solvatochromatic colorants, for instance, are believed to exhibit a detectable color change in the presence of a broad spectrum of microorganisms. More specifically, solvatochromatic colorants may undergo a color change in a certain molecular environment based on solvent polarity and/or hydrogen bonding propensity. For example, a solvatochromatic colorant may be blue in a polar environment (e.g., water), but yellow or red in a non-polar environment (e.g., lipid-rich solution). The color produced by the solvatochromatic colorant depends on the molecular polarity difference between the ground and excited state of the colorant.

Merocyanine colorants (e.g., mono-, di-, and tri-merocyanines) are one example of a type of solvatochromatic colorant that may be employed in the present invention. Merocyanine colorants, such as merocyanine 540, fall within the donor—simple acceptor colorant classification of Griffiths as discussed in "Colour and Constitution of Organic Molecules" Academic Press, London (1976). More specifically, merocyanine colorants have a basic nucleus and acidic nucleus separated by a conjugated chain having an even number of methine carbons. Such colorants possess a carbonyl group that acts as an electron acceptor moiety. The electron acceptor is conjugated to an electron donating group, such as a hydroxyl or amino group. The merocyanine colorants may be cyclic or acyclic (e.g., vinylalogous amides of cyclic merocyanine colorants). For example, cyclic merocyanine colorants generally have the following structure:

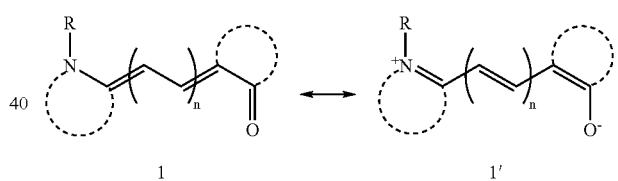

wherein, n is any integer, including 0. As indicated above by the general structures 1 and 1', merocyanine colorants typically have a charge separated (i.e., "zwitterionic") resonance form. Zwitterionic colorants are those that contain both positive and negative charges and are net neutral, but highly charged. Without intending to be limited by theory, it is believed that the zwitterionic form contributes significantly to the ground state of the colorant. The color produced by such colorants thus depends on the molecular polarity difference between the ground and excited state of the colorant. One particular example of a merocyanine colorant that has a ground state more polar than the excited state is set forth below as structure 2.

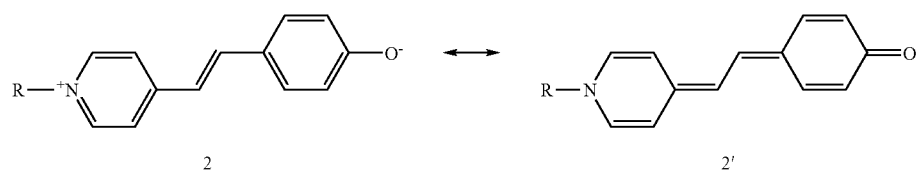

The charge-separated left hand canonical 2 is a major contributor to the ground state whereas the right hand canonical 2' is a major contributor to the first excited state. Still other examples of suitable merocyanine colorants are set forth below in the following structures 3-13.

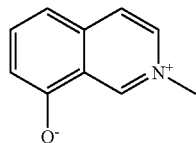

3

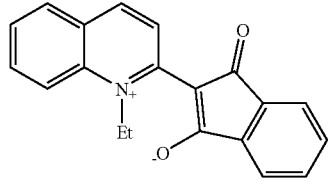

4

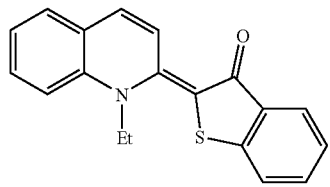

5

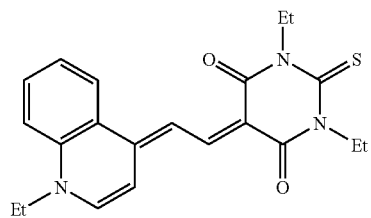

6

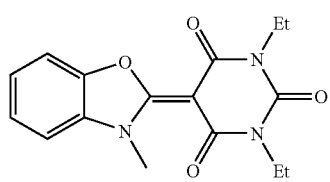

7

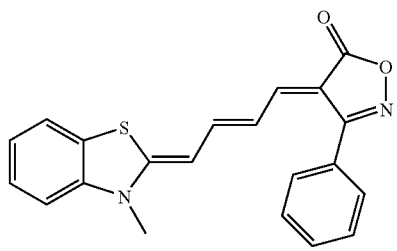

8

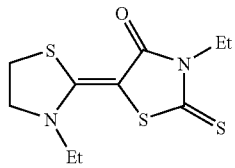

9

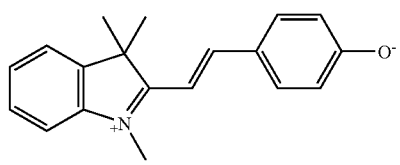

10

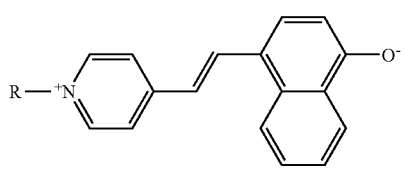

11

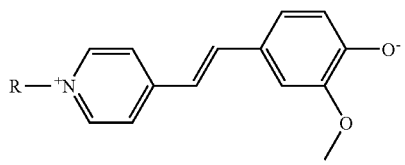

12

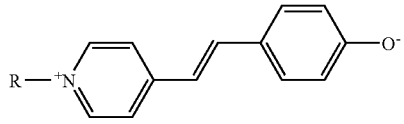

13 wherein, "R" is a group, such as methyl, alkyl, aryl, phenyl, etc.

Indigo is another example of a suitable solvatochromatic colorant for use in the present invention. Indigo has a ground state that is significantly less polar than the excited state. For example, indigo generally has the following structure 14:

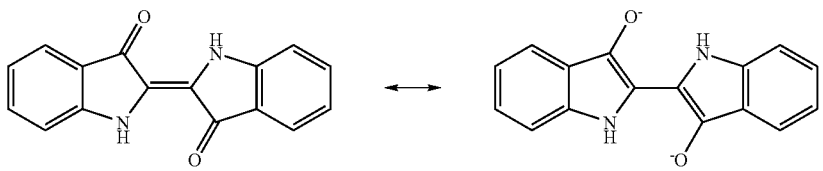

14  14'

The left hand canonical form 14 is a major contributor to the ground state of the colorant, whereas the right hand canonical 14' is a major contributor to the excited state.

Other suitable solvatochromatic colorants that may be used in the present invention include those that possess a permanent zwitterionic form. That is, these colorants have formal positive and negative charges contained within a contiguous π-electron system. Contrary to the merocyanine colorants referenced above, a neutral resonance structure cannot be drawn for such permanent zwitterionic colorants. Exemplary colorants of this class include N-phenolate betaine colorants, such as those having the following general structure:

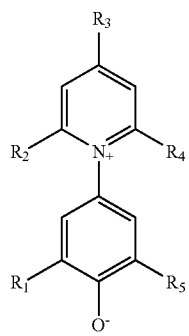

wherein $R_1$-$R_5$ are independently selected from the group consisting of hydrogen, a nitro group (e.g., nitrogen), a halogen, or a linear, branched, or cyclic $C_1$ to $C_{20}$ group (e.g., alkyl, phenyl, aryl, pyridinyl, etc.), which may be saturated or unsaturated and unsubstituted or optionally substituted at the same or at different carbon atoms with one, two or more halogen, nitro, cyano, hydroxy, alkoxy, amino, phenyl, aryl, pyridinyl, or alkylamino groups. For example, the N-phenolate betaine colorant may be 4-(2,4,6-triphenylpyridinium-1-yl)-2,6-diphenylphenolate (Reichardt's dye) having the following general structure 15:

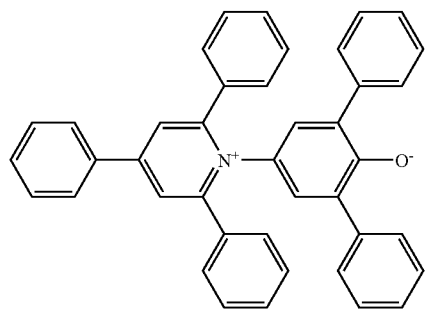

Reichardt's dye shows strong negative solvatochromism and may thus undergo a significant color change from blue to colorless in the presence of bacteria. That is, Reichardt's dye displays a shift in absorbance to a shorter wavelength and thus has visible color changes as solvent eluent strength (polarity) increases. Still other examples of suitable negatively solvatochromatic pyridinium N-phenolate betaine colorants are set forth below in structures 16-23:

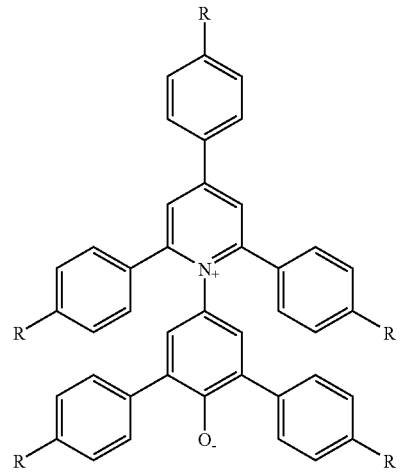

wherein, R is hydrogen, —C(CH$_3$)$_3$, —CF$_3$, or C$_6$F$_{13}$.

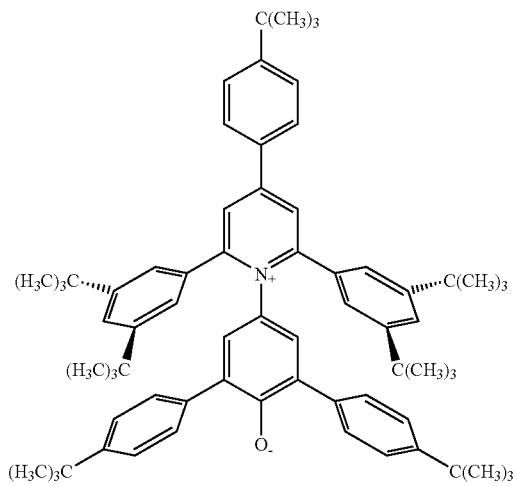

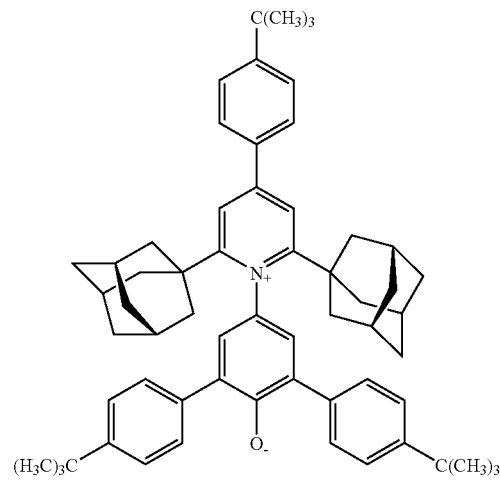

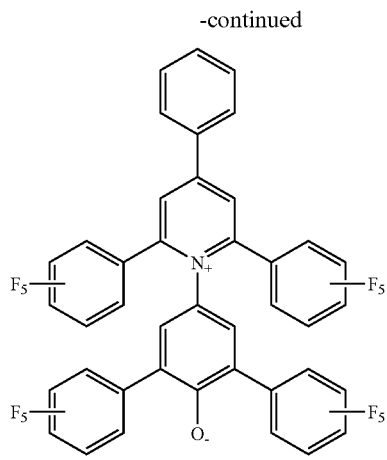
19
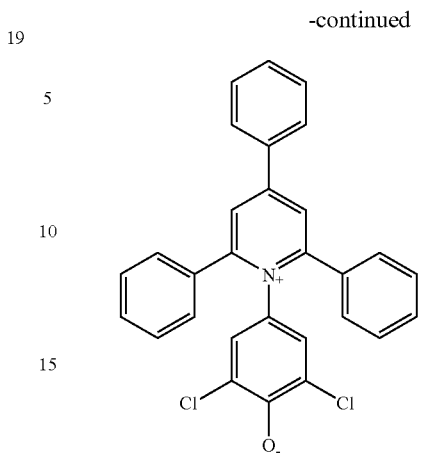
23
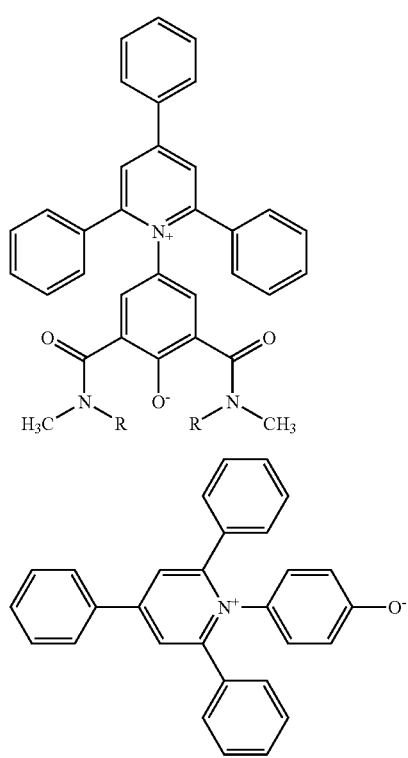
Still additional examples of colorants having a permanent zwitterionic form include colorants having the following general structure 24:
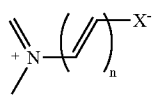
24
wherein, n is 0 or greater, and X is oxygen, carbon, nitrogen, sulfur, etc. Particular examples of the permanent zwitterionic colorant shown in structure 24 include the following structures 25-33.
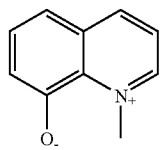
25
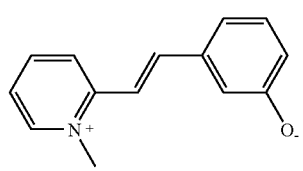
26
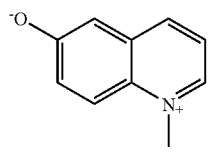
27
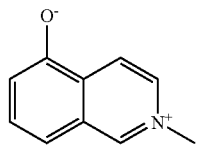
28
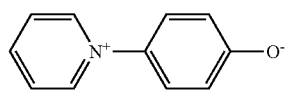
29

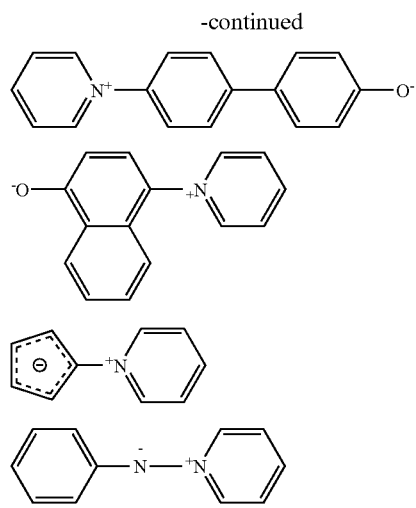

Still other suitable solvatochromatic colorants may include, but are not limited to 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl)julolidine (DCVJ); phenol blue; stilbazolium colorants; coumarin colorants; ketocyanine colorants; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Besides the above-mentioned colorants, still other suitable colorants that may be used in the present invention include, but are not limited to, 4-[2-N-substituted-1,4-hydropyridin-4-ylidine)ethylidene]cyclohexa-2,5-dien-1-one, red pyrazolone colorants, azomethine colorants, indoaniline colorants, and mixtures thereof.

Although the above-referenced colorants are classified based on their mechanism of color change (e.g., pH sensitive, metal complexing, or solvatochromatic), it should be understood that the present invention is not limited to any particular mechanism for the color change. Even when a pH-sensitive colorant is employed, for instance, other mechanisms may actually be wholly or partially responsible for the color change of the colorant. For example, redox reactions between the colorant and microorganism may contribute to the color change.

As stated, the particular selection of colorants is not critical to the present invention so long as the array produces a distinct spectral response. The individual array addresses may be configured in a variety of ways to accomplish this purpose. In one particular embodiment, individual array addresses may contain colorants that each exhibits a spectral response in the presence of a microorganism. For example, one array address may employ a pH-sensitive colorant that undergoes a color change at acidic pH levels, while another array address may contain a pH-sensitive colorant that undergoes a color change at neutral or basic levels. Alternatively, the array addresses may simply contain different chemical classes of colorants, irrespective of the mechanism by which they change color. For instance, a first array address may contain a phthalein colorant, a second array address may contain an aromatic azo colorant, a third array address may contain an anthraquinone colorant, and a fourth array address may contain an arylmethane colorant. Of course, the spectral distinction between individual array addresses need not always be provided by the use of different colorants. For example, the same colorants may be used in individual array addresses, but at a different concentration so as to produce a different spectral response. Certain addresses may likewise contain the same colorant at the same concentration, so long as the array as whole is capable of producing a distinct spectral response.

Apart from the composition of the individual array addresses, a variety of other aspects of the array may be selectively controlled to enhance its ability to provide a distinct spectral response. One factor that influences the ability of the array to produce a distinct spectral response is the number of array addresses employed. Namely, a greater number of individual array addresses may enhance the degree that the spectral response varies for different microorganisms. However, an overly large number of addresses can also lead to difficulty in visually differentiating between spectral responses. Thus, in most embodiments of the present invention, the array contains from 2 to 50 array addresses, in some embodiments from 3 to about 40 array addresses, and in some embodiments, from 4 to 20 array addresses. The number of addresses employed in the array will ultimately depend, at least in part, on the nature of the selected colorants. That is, if the selected colorants have a similar color change in the presence of a microorganism, a larger number of addresses may be needed to provide the desired spectral response.

Another aspect of the array that may influence its ability to provide a distinctive spectral response is the pattern (e.g., size, spacing, alignment, etc.) of the individual array addresses. The individual array addresses may possess a size effective to permit visual observation without unduly increasing the size of the solid support. The width (or diameter) of the addresses may, for example, range from about 0.01 to about 100 millimeters, in some embodiments from about 0.1 to about 50 millimeters, and in some embodiments, from about 1 to about 20 millimeters. The shape of the addresses may also enhance visual observation of the spectral response. For example, the addresses may be in the form of stripes, bands, dots, or any other geometric shape. The addresses may also be spaced apart a certain distance to provide a more visible spectral response. The spacing between two or more individual array addresses may, for example, range from about 0.01 to about 100 millimeters, in some embodiments from about 0.1 to about 50 millimeters, and in some embodiments, from about 1 to about 20 millimeters. The overall pattern of the array may take on virtually any desired appearance.

Figure 1B:
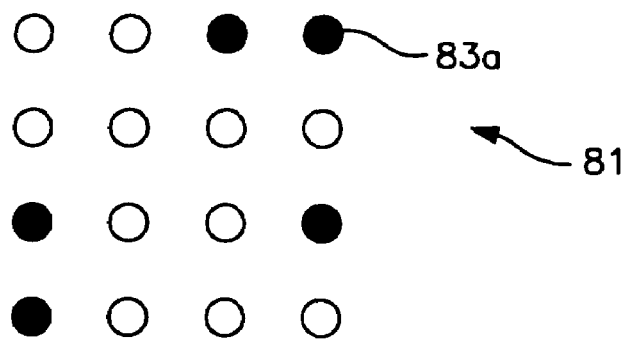
Figure 1C:
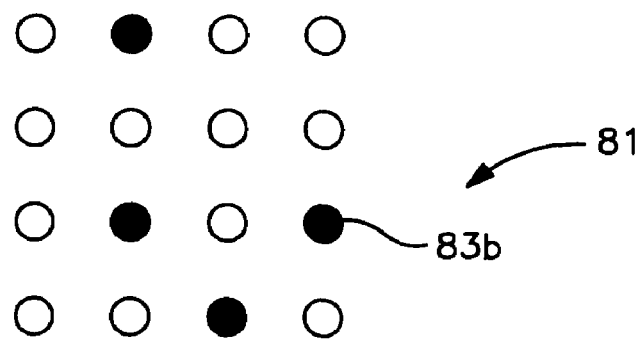

One particular embodiment of the array of the present invention is shown in FIG. 1. As depicted in FIG. 1A, for instance, an array 81 is provided that contains sixteen (16) individual addresses 83 in the form of dots spaced apart in four (4) separate rows and columns. In this embodiment, each of the addresses 83 includes a colorant. For example, a set of first addresses 83a may include colorants that undergo a color change in the presence of E. coli and a set of second addresses 83b may include colorants that undergo a color change in the presence of S. Aureus. When a sample infected with E. coli contacts the array, the first set of addresses 83a undergo a color change, while the second set of addresses 83b remains substantially the same or undergo only a faint color change (FIG. 1B). When a dermal sample infected with S. aureus contacts the array 81, the second set of addresses 83b undergo a color change, while the first set of addresses 83a remains substantially the same or undergo only a faint color change (FIG. 1C).

The array of the present invention is formed on a solid support, which is subsequently contacted with the test sample of interest. The solid support may be formed from any of a variety materials, such as a film, paper, nonwoven web, knitted fabric, woven fabric, foam, glass, etc. For example, the materials used to form the solid support may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth.

Although not required, the colorant may be applied to the solid support in the form of a composition that contains a mobile carrier. The carrier may be a liquid, gas, gel, etc., and may be selected to provide the desired performance (time for change of color, contrast between different areas, and sensitivity) of the colorant. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide, "DMF"); etc.

Other additives may also be incorporated into the array addresses, either separately or in conjunction with the colorant composition. In one embodiment, for instance, cyclodextrins are employed that enhance the sensitivity of the colorant and the contrast between individual array addresses. While not wishing to be bound by theory, the present inventors believe that such additives may inhibit the crystallization of the colorant and thus provide a more vivid color and also enhance detection sensitivity. That is, single colorant molecules have greater sensitivity for microorganisms because each colorant molecule is free to interact with the microbial membrane. In contrast, small crystals of colorant have to first dissolve and then penetrate the membrane. Examples of suitable cyclodextrins may include, but are not limited to, hydroxypropyl-β-cyclodextrin, hydroxyethyl-β-cyclodextrin, γ-cyclodextrin, hydroxypropyl-γ-cyclodextrin, and hydroxyethyl-γ-cyclodextrin, which are commercially available from Cerestar International of Hammond, Ind.

Surfactants may also help enhance the sensitivity of the colorant and the contrast between different addresses. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

A binder may also be employed to facilitate the immobilization of the colorant on the solid support. For example, water-soluble organic polymers may be employed as binders, such as polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable techniques for applying the colorant composition to the solid support in the form of individual array addresses include printing, dipping, spraying, melt extruding, coating (e.g., solvent coating, powder coating, brush coating, etc.), spraying, and so forth. Printing techniques may include, for instance, gravure printing, flexographic printing, screen printing, laser printing, thermal ribbon printing, piston printing, etc. In one particular embodiment, ink-jet printing techniques are employed to form the array on the support. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

The colorant composition may be formed as a printing ink using any of a variety of known components and/or methods. For example, the printing ink may contain water as a carrier, and particularly deionized water. Various co-carriers may also be included in the ink, such as lactam, N-methylpyrrolidone, N-methylacetamide, N-methylmorpholine-N-oxide, N,N-dimethylacetamide, N-methyl formamide, propyleneglycol-monomethylether, tetramethylene sulfone, tripropyleneglycolmonomethylether, propylene glycol, and triethanolamine (TEA). Humectants may also be utilized, such as ethylene glycol; diethylene glycol; glycerine; polyethylene glycol 200, 300, 400, and 600; propane 1,3 diol; propyleneglycolmonomethyl ethers, such as Dowanol PM (Gallade Chemical Inc., Santa Ana, Calif.); polyhydric alcohols; or combinations thereof. Other additives may also be included to improve ink performance, such as a chelating agent to sequester metal ions that could become involved in chemical reactions over time, a corrosion inhibitor to help protect metal components of the printer or ink delivery system, and a surfactant to adjust the ink surface tension. Various other components for use in an ink, such as colorant stabilizers, photoinitiators, binders, surfactants, electrolytic salts, pH adjusters, etc., may be employed as described in U.S. Pat. No. 5,681,380 to Nohr, et al. and U.S. Pat. No. 6,542,379 to Nohr, et al., which are incorporated herein in their entirety by reference thereto for all purposes.

The exact quantity of a colorant employed within an array address may vary based on a variety of factors, including the sensitivity of the colorant, the presence of other additives, the desired degree of detectability (e.g., with an unaided eye), the suspected concentration of the microorganism, etc. In some cases, it is desirable to only detect the presence of microorganisms at concentrations that are certain threshold concentrations (e.g., pathogenic). For example, a concentration of about $1 \times 10^3$ colony forming units ("CFU") per milliliter of a test sample or more, in some embodiments about $1 \times 10^5$ CFU/ml or more, in some embodiments about $1 \times 10^6$ CFU/ml or more, and in some embodiments, about $1 \times 10^7$ CFU/ml or more of a microorganism may be detected in the present invention. Thus, colorants may be employed in an amount sufficient to undergo a detectable color change in the presence of a microorganism at a concentration of at least about $1 \times 10^3$ CFU per milliliter of the test sample. For instance, the colorant may be applied at a concentration from about 0.1 to about 100 milligrams per milliliter of carrier, in some embodiments from about 0.5 to about 60 milligrams per milliliter of carrier, and in some embodiments, from about 1 to about 40 milligrams per milliliter of carrier.

The spectral response of the array of the present invention provides information regarding the presence of a microorganism to which it is exposed. If desired, the response of a reacted array may be compared (e.g., visually or with the aid of an instrument) to a control array, which is formed in a manner that is the same or similar to the test array with respect to its responsiveness to microorganisms. Multiple control arrays may likewise be employed that correspond to different types of microorganisms at a certain concentration. Upon comparison, the microorganism may be identified by selecting the control array having a spectral response that is the same or substantially similar to the response of the reacted test array, and then correlating the selected control array to a particular microorganisms or class of microorganisms. In addition, the array itself may contain one or more colorants that do not generally undergo a detectable color change in the presence of the microorganism so that the colorant(s) may be used for comparative or control purposes.

The spectral response of the array may be determined either visually or using instrumentation. In one embodiment, color intensity is measured with an optical reader. The actual configuration and structure of the optical reader may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the colorant. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Optical readers may generally employ any known detection technique, including, for instance, luminescence (e.g., fluorescence, phosphorescence, etc.), absorbance (e.g., fluorescent or non-fluorescent), diffraction, etc. In one particular embodiment of the present, the optical reader measures color intensity as a function of absorbance. In one embodiment, absorbance readings are measured using a microplate reader from Dynex Technologies of Chantilly, Va. (Model # MRX). In another embodiment, absorbance readings are measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, $L^*$, $a^*$, and $b^*$, which correspond to three characteristics of a perceived color based on the opponent theory of color perception. The three variables have the following meaning:

$L^*$=Lightness (or luminosity), ranging from 0 to 100, where 0=dark and 100=light;

$a^*$=Red/green axis, ranging approximately from $-100$ to 100; positive values are reddish and negative values are greenish; and $b^*$=Yellow/blue axis, ranging approximately from $-100$ to 100; positive values are yellowish and negative values are bluish.

Because CIELAB color space is somewhat visually uniform, a single number may be calculated that represents the difference between two colors as perceived by a human. This difference is termed $\Delta E$ and calculated by taking the square root of the sum of the squares of the three differences ($\Delta L^*$, $\Delta a^*$, and $\Delta b^*$) between the two colors. In CIELAB color space, each $\Delta E$ unit is approximately equal to a "just noticeable" difference between two colors. CIELAB is therefore a good measure for an objective device-independent color specification system that may be used as a reference color space for the purpose of color management and expression of changes in color. Using this test, color intensities ($L^*$, $a^*$, and $b^*$) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still another suitable optical reader is the reflectance spectrophotometer described in U.S. Patent App. Pub. No. 2003/0119202 to Kaylor, et al., which is incorporated herein in its entirety by reference thereto for all purposes. Likewise, transmission-mode detection systems may also be used in the present invention.

As a result of the present invention, it has been discovered that microorganism contamination may be detected through the use of a array that produces a distinct spectral response for a microorganism or class or microorganisms. The microorganisms that may be detected in accordance with the present invention are not particularly limited, and may include bacteria, yeast, fungi, mold, protozoa, viruses, etc. Several relevant bacterial groups that may be detected in the present invention include, for instance, gram negative rods (e.g., Entereobacteria); gram negative curved rods (e.g., vibious, *Heliobacter, Campylobacter*, etc.); gram negative cocci (e.g., *Neisseria*); gram positive rods (e.g., *Bacillus, Clostridium*, etc.); gram positive cocci (e.g., *Staphylococcus, Streptococcus*, etc.); obligate intracellular parasites (e.g., *Ricckettsia* and *Chlamydia*); acid fast rods (e.g., *Myobacterium, Nocardia*, etc.); spirochetes (e.g., *Treponema, Borellia*, etc.); and mycoplasmas (i.e., tiny bacteria that lack a cell wall). Particularly relevant bacteria include *E. coli* (gram negative rod), *Klebsiella pneumonia* (gram negative rod), *Streptococcus* (gram positive cocci), *Salmonella choleraesuis* (gram negative rod), *Staphyloccus aureus* (gram positive cocci), and *P. aeruginosa* (gram negative rod).

In addition to bacteria, other microorganisms of interest include molds and yeasts (e.g., *Candida albicans*), which belong to the Fungi kingdom. Zygomycota, for example, is a class of fungi that includes black bread mold and other molds that exhibit a symbiotic relationship with plants and animals. These molds are capable of fusing and forming tough "zygospores." Ascomycota is another class of fungi, which includes yeasts, powdery mildews, black and blue-green molds, and some species that cause diseases such as Dutch elm disease, apple scab, and ergot. The life cycle of these fungi combines both sexual and asexual reproduction, and the hyphae are subdivided into porous walls that allow for passage of the nuclei and cytoplasm. Deuteromycota is another class of fungi that includes a miscellaneous collection of fungi that do not fit easily into the aforementioned classes or the Basidiomycota class (which includes most mushrooms, pore fungi, and puffball fungi). Deuteromycetes include the species that create cheese and penicillin, but also includes disease-causing members such as those that lead to athlete's foot and ringworm.

Regardless, the spectral response of the array of the present invention is rapid and may be detected within a relatively short period of time. For example, the spectral response may occur in about 20 minutes or less, in some embodiments about 10 minutes or less, in some embodiments about 5 minutes or less, in some embodiments about 3 minutes or less, and in some embodiments, from about 10 seconds to about 2 minutes. In this manner, the array may provide a "real-time" indication of the presence or absence of a microorganism or class of microorganisms.

The present invention may be better understood with reference to the following examples.

EXAMPLES

Materials Employed

All reagents and solvents were obtained from Sigma-Aldrich Chemical Company, Inc. of St. Louis, Mo. unless otherwise noted and were used without further purification. The microorganisms used in the study were:

1. Gram Negative (Viable)
*Escherichia coli* (ATCC #8739) (*E. coli*)
*Psuedomonas aeruginosa* (ATCC #9027) (*P. aeruginosa*)
*Klebsiella pneumoniae* (ATCC #4352) (*K. pneumoniae*)
*Proteus mirabilis* (ATCC #7002) (*P. mirabilis*)
*Haemophilus influenzae* (ATCC #49247) (*H. influenzae*)
*Moraxella lacunata* (ATCC #17972) (*M. lacunata*)
2. Gram Positive (Viable)
*Staphylococcus aureus* (ATCC #6538) (*S. aureus*)
*Lactobacillus acidophilus* (ATCC #11975) (*L. acidophilus*)
*Staphylococcus epidermidis* (ATCC #12228) (*S. epidermidis*)

*Bacillus subtilis* (ATCC #19659) (*B. subtilis*)
*Enterococcus faecalis* (ATCC #29212) (*E. faecalis*)
*Streptococcus pyogenes* (ATCC #10782) (*S. pyogenes*)
*Streptococcus pneumoniae* (ATCC #10015) (*S. pneumoniae*)
3. Yeast (Viable)
*Candida albicans* (ATCC #10231) (*C. albicans*)

4. Mold (Viable)
*Aureobasidium pullulans* (ATCC #16622) (*A. pullulans*)
*Penicillium janthinellum* (ATCC #10069) (*P. janthinellum*)

The colorants used in the study are listed with their molecular structure in Table 1:

TABLE 1

Exemplary Colorants and Their Corresponding Structure

| Colorant | Structure |
|---|---|
| 4-[(1-Methyl-4(1H)-pyridinylidene)ethylidene]-2,5-cyclohexadien-1-one hydrate | 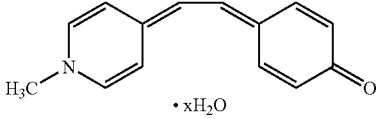 |
| 3-Ethyl-2-(2-hydroxy-1-propenyl)benzothiazolium chloride | 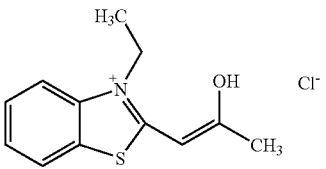 |
| 1-Docosyl-4-(4-hydroxystyryl)pyridinium bromide | 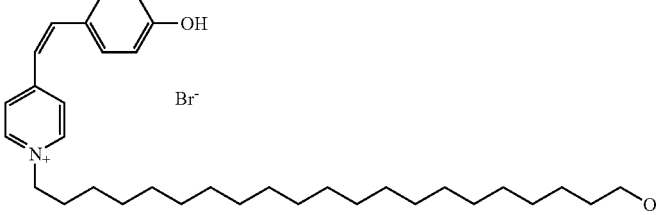 |
| N,N-Dimethylindoaniline | 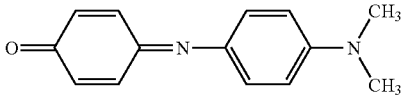 |
| Quinalizarin | 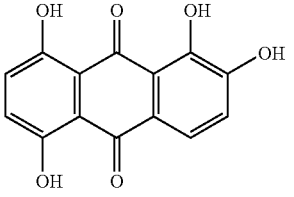 |
| Merocyanine 540 | 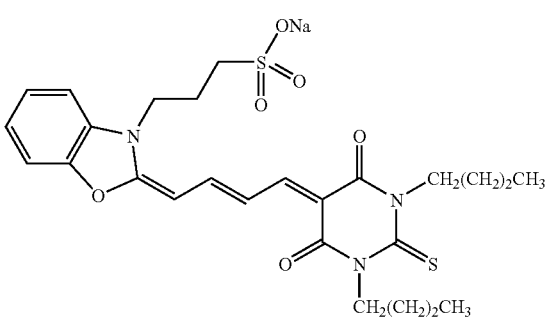 |

TABLE 1-continued

Exemplary Colorants and Their Corresponding Structure

| Colorant | Structure |
|---|---|
| Eriochrome Blue SE | 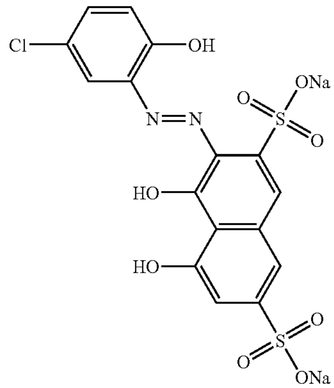 |
| Phenol Red | 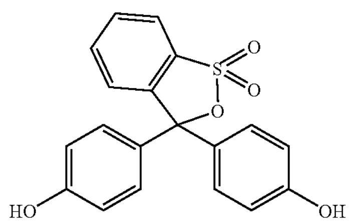 |
| Nile Blue A | 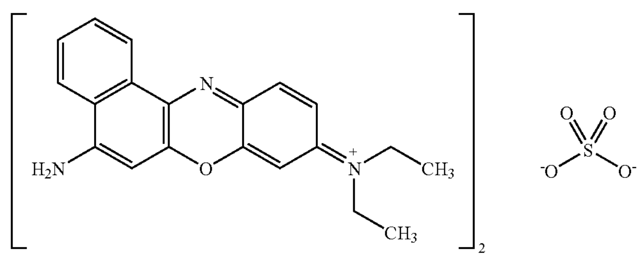 |
| 1-(4-Hydroxyphenyl)-2,4,6-triphenylpyridinium hydroxide inner salt hydrate | 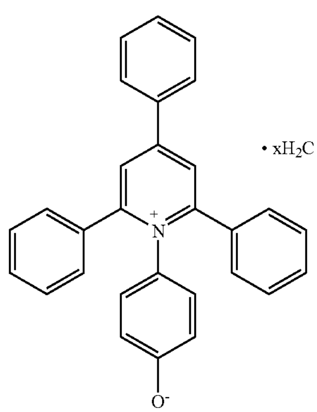 |

TABLE 1-continued

Exemplary Colorants and Their Corresponding Structure

| Colorant | Structure |
| --- | --- |
| Azomethine-H monosodium salt hydrate | 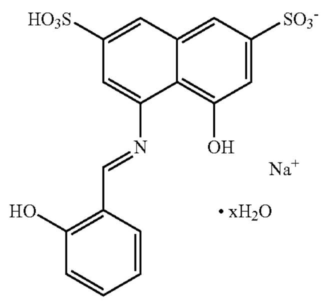 |
| Indigo carmine | 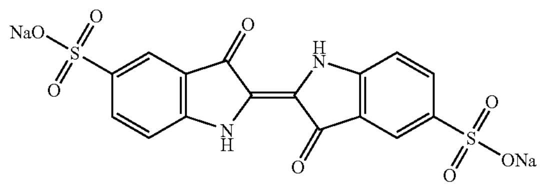 |
| Methylene Violet | 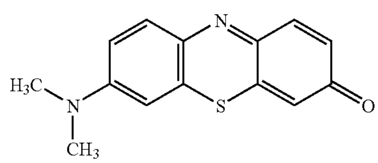 |
| Eriochrome Blue Black B | 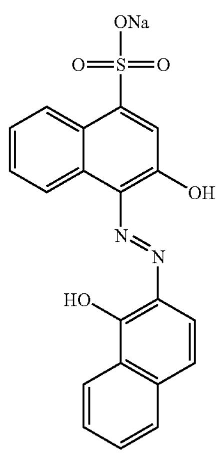 |
| Methylene Blue | 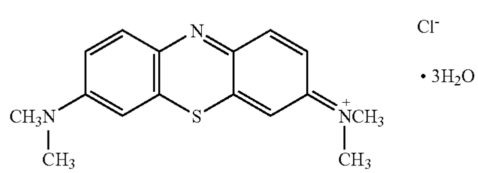 |
| Nile Red | 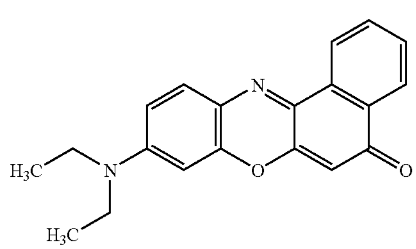 |

TABLE 1-continued

Exemplary Colorants and Their Corresponding Structure

| Colorant | Structure |
| --- | --- |
| Trypan Blue | 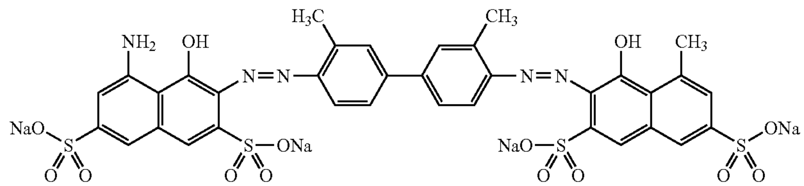 |
| Safranin O | 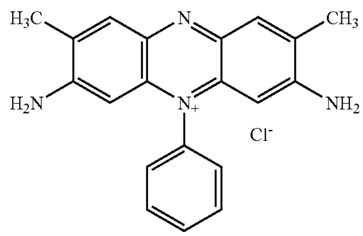 |
| Crystal Violet | 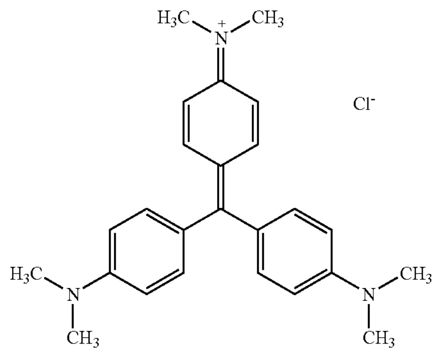 |
| Methyl Orange | 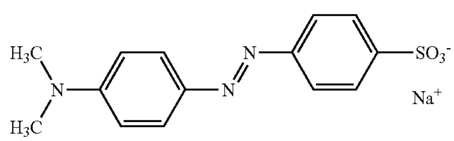 |
| Chrome Azurol S | 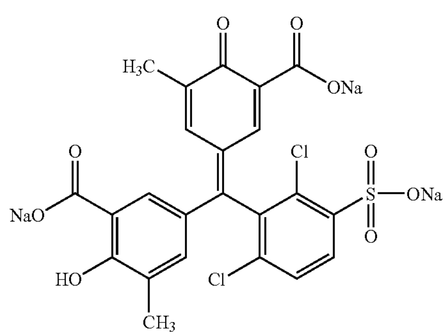 |
| Leucocrystal violet | 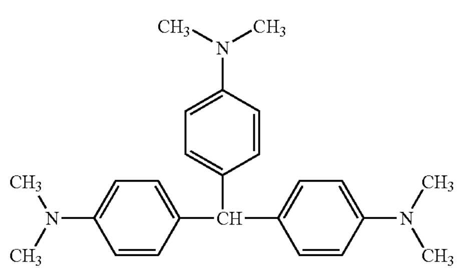 |

TABLE 1-continued

Exemplary Colorants and Their Corresponding Structure

| Colorant | Structure |
| --- | --- |
| Leucomalachite Green | 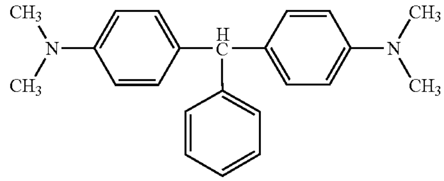 |
| Leuco xylene cyanole FF | 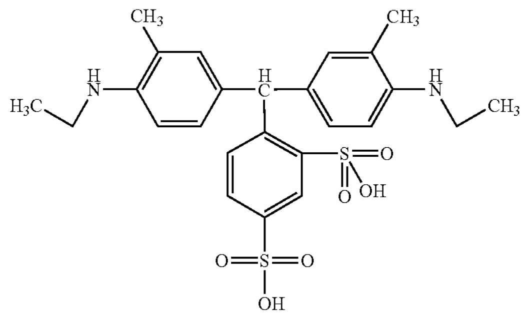 |
| 4,5-Dihydroxy-1,3-benzenedisulfonic acid disodium salt monohydrate | 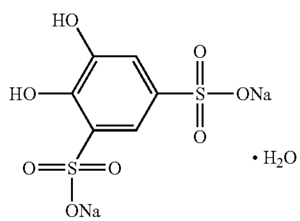 |
| 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt | 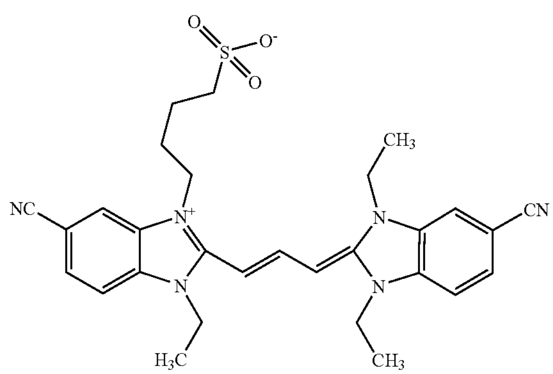 |
| Acid Green 25 | 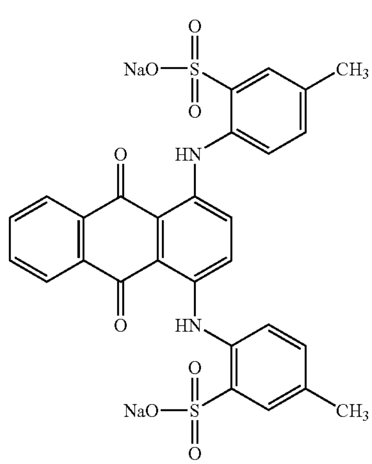 |

TABLE 1-continued

Exemplary Colorants and Their Corresponding Structure

| Colorant | Structure |
| --- | --- |
| Bathophenanthrolinedisulfonic acid disodium salt trihydrate | 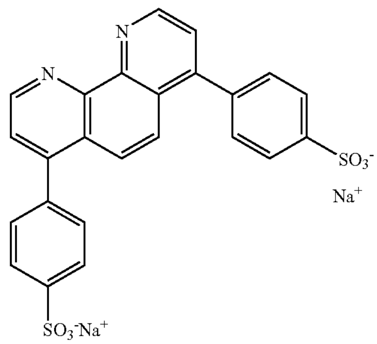 |
| Carminic Acid | 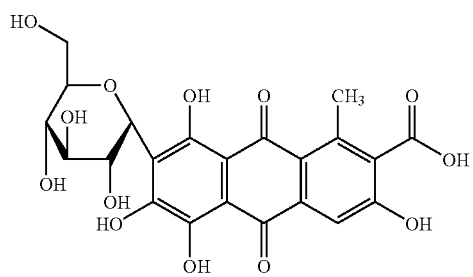 |
| Celestine Blue | 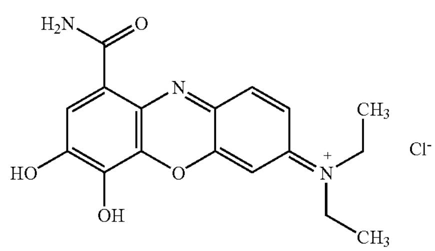 |
| Hematoxylin | 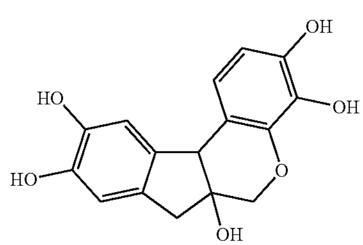 |
| Bromophenol Blue | 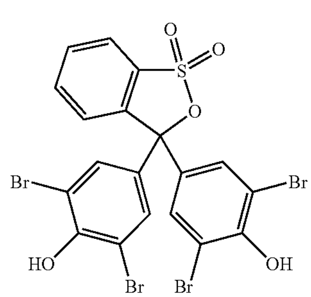 |

TABLE 1-continued

Exemplary Colorants and Their Corresponding Structure

| Colorant | Structure |
|---|---|
| Bromothymol blue | 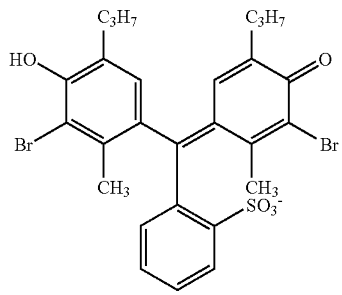 |
| Rose Bengal | 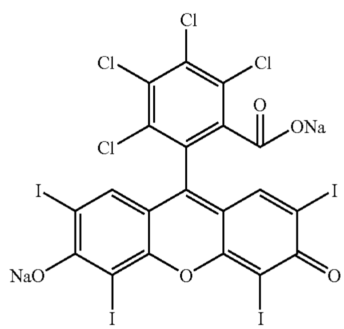 |
| Universal indicator 0-5 | Not available |
| Universal indicator 3-10 | Not available |
| Alizarin Complexone | 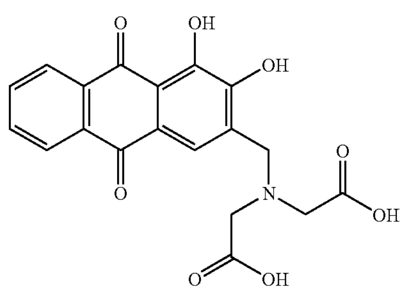 |
| Alizarin Red S | 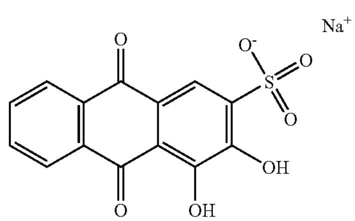 |
| Purpurin | 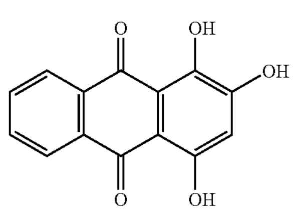 |

TABLE 1-continued
Exemplary Colorants and Their Corresponding Structure
| Colorant | Structure |
| --- | --- |
| Alizarin | 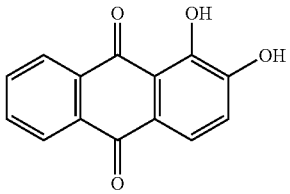 |
| Emodin | 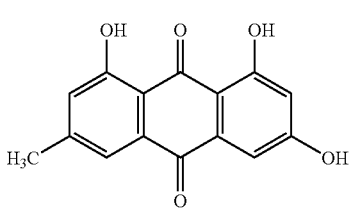 |
| Amino-4-hydroxyanthraquinone | 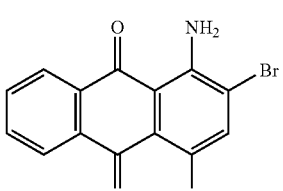 |
| Nuclear Fast Red | 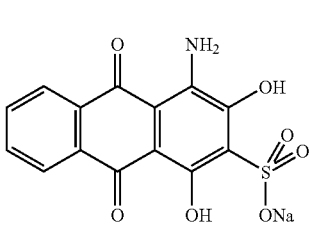 |
| Chlorophenol Red | 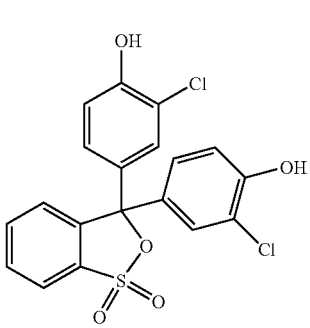 |
| Remazol Brilliant Blue R | 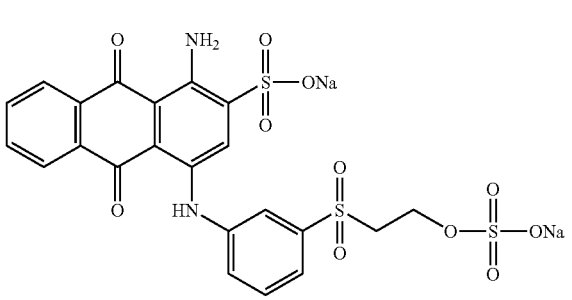 |

TABLE 1-continued

Exemplary Colorants and Their Corresponding Structure

| Colorant | Structure |
|---|---|
| Procion Blue HB | 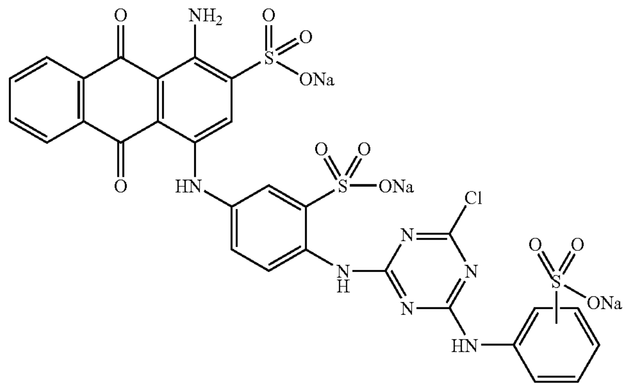 |
| Phenolphthalein | 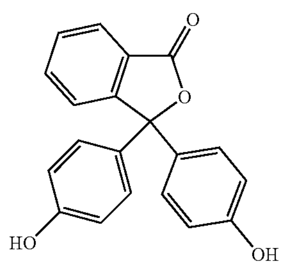 |
| Ninhydrin | 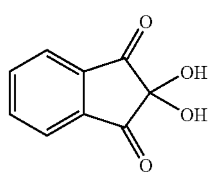 |
| Nitro blue tetrazolium | 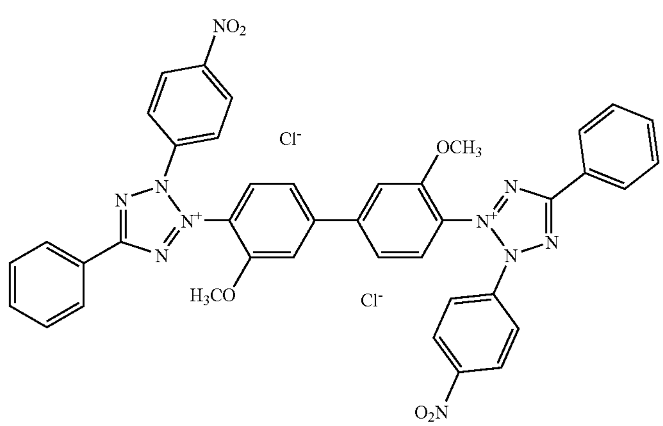 |

TABLE 1-continued

Exemplary Colorants and Their Corresponding Structure

| Colorant | Structure |
|---|---|
| Orcein | (structure shown) |
| Celestine blue | (structure shown) |
| Tetra Methyl-para-phenylene diamine (TMPD) | (structure shown) |
| 5,10,15,20-Tetrakis(pentafluorophenyl) porphyrin iron(III) chloride | (structure shown) |

Example 1

Various colorants were tested for their ability to undergo a color change in the presence of S. aureus, E. coli, and C. albicans microorganisms. The colorants tested were Reichardt's dye, 1-Docosyl-4-(4-hydroxystyryl)pyridinium bromide, 3-Ethyl-2-(2-hydroxy-1-propenyl)-benzothiazolium chloride, 4-[(1-Methyl-4(1H)-pyridinylidene)ethylidene]-2,5-cyclohexadien-1-one hydrate, N,N-Dimethylindoaniline, Quinalizarin, Merocyanine 540, Eriochrome® Blue SE (Plasmocorinth B), Phenol Red, Nile Blue A, 1-(4-Hydroxyphenyl)-2,4,6-triphenylpyridinium hydroxide inner salt hydrate, Azomethine-H monosodium salt hydrate, Indigo Camine, Methylene Violet, Eriochrome® Blue Black B, Biebrich scarlet-acid fuchsin solution, Methylene Blue, Nile Red, Trypan Blue, Safranin O, Crystal Violet, Methyl Orange, and Chrome Azurol S.

Unless otherwise specified, the colorants were dissolved in dimethylformamide (DMF). The colorant solutions were then pipetted onto 15-cm filter paper (available from VWR International—Catalog No. 28306-153) and allowed to dry. The filter paper was sectioned into quadrants to test four (4) samples—i.e., S. aureus, E. coli, C. albicans, and sterile water. 100 microliters of $10^7$ CFU/mL of S. aureus was pipetted onto the filter paper in one quadrant, 100 microliters of $10^7$ CFU/mL of E. coli was pipetted onto the filter paper in a second quadrant, 100 microliters of $10^6$ CFU/mL of C. albicans was pipetted onto the filter paper in a third quadrant, and sterile water was pipetted in the final quadrant. Color changes in the colorants were observed and recorded for each of the samples tested. The color was recorded immediately after the color change to inhibit the fading (or loss of intensity) of the colors as the samples dried. Table 2 presents the observations from the experiment.

TABLE 2

Observations of Colorant Color Change (Group 1)

| Colorant | Initial Color | Color Change w/ *S. aureus* | Color Change w/ *E. coli* | Color Change w/ *C. albicans* | Color Change w/ sterile water |
|---|---|---|---|---|---|
| Reichardt's dye | Blue | Colorless | Colorless | Colorless | No change |
| 1-Docosyl-4-(4-hydroxystyryl)pyridinium bromide | Yellow | Very faint orange | Faint orange | Faint orange | Very faint orange |
| 3-Ethyl-2-(2-hydroxy-1-propenyl)benzothiazolium chloride, | White/cream | No change | No change | No change | No change |
| 4-[(1-Methyl-4(1H)-pyridinylidene)ethylidene]-2,5-cyclohexadien-1-one hydrate | Bright yellow | No change | No change | No change | No change |
| N,N-Dimethylindoaniline | Grey | Faint pink | Very faint pink | Very faint pink | No change |
| Quinalizarin | Peach | Yellow | Faint purple | Purple | No change |
| Merocyanine 540 | Hot pink | Light purple | Yellowish pink | Deeper yellowish pink | Reddish pink |
| Eriochrome Blue SE (Plasmocorinth B) | Deep pink | Very faint purple | Purple | Deep purple | Lighter pink with dark pink border (dissolution) |
| Phenol Red | Yellow | Yellow with orange border | Orange | Deep red/orange | Green with orange border |
| Nile Blue A | Blue | Pink | Pink | Pink | No change |
| 1-(4-Hydroxyphenyl)-2,4,6-triphenylpyridinium hydroxide inner salt hydrate | Yellow | No change | No change | No change | No change |
| Azomethine-H monosodium salt hydrate | Yellow/peach | Lighter with deeper border (dissolution) | Lighter with deeper border (dissolution) | Lighter with deeper border (dissolution) | Lighter with deeper border (dissolution) |
| Indigo Carmine | Light blue | Deeper light blue | Deeper light blue | Deeper light blue | Light blue with deeper border (dissolution) |
| Methylene Violet | Deep blue/violet | Deeper blue | Deeper blue | Deeper blue | No change |
| Eriochrome ® Blue Black B | Dark muddy purple | Lighter muddy purple | Deep purple | Deep blue | Darker muddy purple |
| Biebrich scarlet-acid fuchsin solution | Bright red | Lighter with deeper border (dissolution) | Lighter with deeper border (dissolution) | Lighter with deeper border (dissolution) | Lighter with deeper border (dissolution) |
| Methylene Blue* | Bright blue | No change | No change | No change | No change |
| Nile Red | Bright purple | Light pink | Light pink | Light pink | Faint pink |
| Trypan Blue* | Deep blue | No change | No change | No change | Faintly lighter with deeper border (dissolution) |
| Safranin O | Bright salmon | Yellowish with salmon edge | Yellowish with salmon edge | Yellowish with salmon edge | Pinkish with salmon edge |
| Crystal Violet | Deep blue | No change | No change | No change | Faintly lighter with deeper border (dissolution) |
| Methyl Orange | Bright orange | Yellow | Yellow | Yellow | Lighter orange with dark orange border (dissolution) |
| Chrome Azurol S | Pink | Light orange with dark orange border | Light yellow with dark pink border | Brighter yellow with dark pink border | Light pink with dark pink border |

*Dissolved in water

With the exception of Methyl Orange, Nile Red, and Merocyanine 540, the observed color change was almost immediate (1 to 2 minutes).

Example 2

Various colorants were tested for their ability to undergo a color change in the presence of *S. aureus, E. coli*, and *C. albicans* microorganisms. The colorants tested were Leucocrystal Violet, Leucomalachite Green, Leuco xylene cyanole FF, 4,5-Dihydroxy-1,3-benzenedisulfonic acid disodium salt monohydrate, 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt, Acid Green 25, Bathophenanthrolinedisulfonic acid disodium salt trihydrate, Carminic Acid, Celestine Blue, Hematoxylin, Bromophenol Blue, Bromothymol Blue, Rose Bengal, Universal Indicator (0-5), and Universal Indicator (3-10). Unless otherwise specified, the colorants were dissolved in dimethylformamide (DMF). The VWR filter paper and colorants were prepared as described in Example 1. Table 3 presents the observations from the experiment.

TABLE 3

Observations of Colorant Color Change (Group 2)

| Colorant | Initial Color | Color Change w/*S. aureus* | Color Change w/*E. coli* | Color Change w/*C. albicans* | Color Change w/sterile water |
|---|---|---|---|---|---|
| Leucocrystal violet | White | Blue | Blue | Blue | No change |
| Leucomalachite Green | White | Green | Green | Green | No change |
| Leuco xylene cyanole FF | White | No change | No change | No change | No change |
| 4,5-Dihydroxy-1,3-benzenedisulfonic acid disodium salt monohydrate* | White | No change | No change | No change | No change |
| 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt | Bright reddish pink | Dark pink | Dark purplish pink | Dark greenish pink | Lighter pink with dark pink border (dissolution) |
| Acid Green 25 | Green | Lighter green with darker green border (dissolution) | Lighter green with darker green border (dissolution) | Lighter green with darker green border (dissolution) | Lighter green with darker green border (dissolution) |
| Bathophenanthrolinedisulfonic acid disodium salt trihydrate** | White | No change | No change | No change | No change |
| Carminic Acid* | Reddish peach | Pale purple | Purple | Dark purple | Lighter peach with darker peach border (dissolution) |
| Celestine Blue | Dark lavender | Blue | Blue | Blue | Blue |
| Hematoxylin | Pale yellow | No change | Light purple | Darker purple | Pale yellow with darker yellow border (dissolution) |
| Bromophenol Blue | Bright Yellow | Dark blue | Dark blue | Dark blue | Lighter yellow with orangeish border (dissolution) |
| Bromothymol Blue | Yellow | Lighter yellow with darker yellow border | Light green | Darker green | Very light yellow/whitish with darker yellow border |
| Rose Bengal | Hot pink | Darker pink | Purplish pink | Reddish pink | White with dark pink border (dissolution) |
| Universal Indicator (0–5) | Yellowish green | Yellowish blue | Yellowish blue | Yellowish blue | Lighter green with dark green border (dissolution) |
| Universal Indicator (3–10) | Peach | Pinkish peach | Orange-ish yellow | Yellow | Dark peach |

*Dissolved in water
**Dissolved in DMF and water

With the exception of Leucocrystal Violet, Leucomalachite Green, and Leuco xylene cyanole FF, the observed color change was almost immediate (1 to 2 minutes).

Example 3

Various colorants were tested for their ability to undergo a color change in the presence of *S. aureus, E. coli,* and *C. albicans* microorganisms. The colorants tested were Alizarin Complexone, Alizarin Red S, Purpurin, Alizarin, Emodin, Amino-4-hydroxyanthraquinone, Nuclear Fast Red, Chlorophenol Red, Remazol Brilliant Blue R, Procion Blue HB, Phenolphthalein, tetraphenylporphine, tetra-o-sulphonic acid, and Ninhydrin. Unless otherwise specified, the colorants were dissolved in dimethylformamide (DMF). The VWR filter paper and colorants were prepared as described in Example 1. Table 4 presents the observations from the experiment.

Examples 1-3 was demonstrated. Additional colorants were also tested, including Plasmocorinth B, Nitro Blue, Alizarin Complexone, Orcein, Tetra Methyl-para-phenylene diamine (TMPD), Nile Red, Eriochrome Blue Black B, Phenol Red, Alizarin Red S, Carminic Acid, Fe(III)C$_3$, Celestine Blue, Kovac's Reagent, Chrome Azurol S, Universal Indicator 3-10, Methyl Orange, Merocyanine 540, and Iron III Chloride Porphyrin. The gram-positive microorganisms tested were *S. aureus, L. acidophilus, S. epidermidis, B. subtilis,* and *E. faecalis*. The gram-negative microorganisms tested were *E. coli, P. aeruginosa, K. pneumoniae,* and *P. mirabilis*.

The colorant samples were prepared in a manner similar to Example 1. Unless otherwise specified, the colorants were dissolved in dimethylformamide (DM F). Each of the colorant solutions were pipetted onto two separate pieces of VWR filter paper and allowed to dry. One filter paper sample with the dried colorant was sectioned into five approximately equal sections to test the five gram-positive microorganisms.

TABLE 4

Observations of Colorant Color Change (Group 3)

| Colorant | Initial Color | Color Change w/*S. aureus* | Color Change w/*E. coli* | Color Change w/*C. albicans* | Color Change w/sterile water |
|---|---|---|---|---|---|
| Alizarin Complexone | Yellow | Brown | Reddish purple | Purple | No change |
| Alizarin Red S | Yellow | Orangeish brown | Pinkish purple | Purple | Lighter yellow with darker yellow border (dissolution) |
| Purpurin | Peachish orange | Darker peachish orange | Reddish pink | Deeper reddish pink | Yellowish peach |
| Alizarin | Butter yellow | No change | Light brown | Purplish brown | Greenish butter yellow |
| Emodin | Yellow | No change | Faint Greenish orange | Deeper greenish orange | Greenish yellow |
| Amino-4-hydroxyanthraquinone | Pink | Lighter pink | Slightly lighter pink | Faintly lighter pink | Darker pink |
| Nuclear Fast Red | Reddish pink | Deeper reddish pink | Yellowish pink | Yellowish pink | Dark pink |
| Chlorophenol Red | Orange-ish yellow | Brown | Deep reddish purple | Deeper reddish purple | Lighter orangish yellow with darker border (dissolution) |
| Remazol Brilliant Blue R | Bright blue | Lighter blue with dark blue border (dissolution) | Lighter blue with dark blue border (dissolution) | Lighter blue with dark blue border (dissolution) | Lighter blue with dark blue border (dissolution) |
| Procion Blue HB | Teal green | No change | No change | Faintly darker teal | Lighter teal with darker border (dissolution) |
| Phenolphthalein | White | No change | No change | No change | No change |
| Tetraphenylporphine, tetra-o-sulphonic acid | Black | Grey with darker borders (dissolution) | Grey with darker borders (dissolution) | Grey with darker borders (dissolution) | Grey with darker borders (dissolution) |
| Ninhydrin | White | Deep purple | Deep purple | Slightly lighter deep | No change |

The observed color change was almost immediate (1 to 2 minutes).

Example 4

The ability to rapidly detect various gram-positive and gram-negative microorganisms utilizing the colorants of The other filter paper sample was sectioned into quadrants to test the four gram negative microorganisms. 100 microliters of 10$^7$ CFU/mL of each microorganism sample was pipetted into their respective section of the sample of filter paper. Table 5 presents the observations from the gram positive microorganisms and Table 6 presents the observations from the gram negative microorganisms.

TABLE 5

Color Change Observations for Gram Positive Microorganisms

| Colorant | Initial Color | Color Change w/B. subtilis | Color Change w/S. aureus | Color Change w/S. epidermidis | Color Change w/ E. faecalis | Color Change w/L. acidophilus |
|---|---|---|---|---|---|---|
| Plasmocorinth B | Deep pink | Purplish pink | Very faint purplish pink | Deeper pink | Reddish pink | Deeper reddish pink |
| Nitro Blue Tetrazolium | Yellowish white | No change | No change | No change | No change | No change |
| Alizarin Complexone | Yellow | Brownish red | Lighter brownish red | Lighter brownish red | Lighter brownish red | Brownish yellow |
| Orcein | Muddy purple | Light purple | Lighter muddy purple | Darker muddy purple | Darker muddy purple | Darker muddy purple |
| Tetra Methyl-para-phenylene diamine (TMPD)* | Bright lavender | Colorless | Colorless | Not tested | Not tested | Colorless |
| Nile Red | Bright purple | Light pink | Light pink | Light pink | Light pink | Light pink |
| Eriochrome Blue Black B | Dark Muddy purple | Bluish purple | Lighter muddy purple | Darker muddy purple | Darker muddy purple | Darker muddy purple |
| Phenol Red | Yellow | Orange with yellowish center | Yellow with orange border | Yellow with orange border | Yellow with orange border | Greenish yellow with orange border |
| Alizarin Red S | Yellow | Brownish pink | Light brown | Light brown | Light brown | Light Greenish brown |
| Carminic Acid* | Reddish peach | Pale purple | Paler purple | Paler purple | Purplish peach | Yellowish peach |
| Fe(III)C₃ | White | No change | No change | Not tested | Not tested | No change |
| Celestine Blue | Dark lavender | Blue | Blue | Blue | Blue | Blue |
| Kovac's Reagent | Pale yellow | White with greenish center and yellow border | White with greenish center and yellow border | White with greenish center and yellow border | White with greenish center and yellow border | White with greenish center and brown border |
| Chrome Azurol S | Pink | Pale yellow with reddish border | Light orange with dark orange border | Light yellowish orange with dark orange border | Light orange with dark orange border | Light red with dark red border |
| Universal Indicator 3–10 | Peach | Lighter peach with yellow center | Lighter peach with yellow center | Lighter peach with yellow center | Lighter peach | Red |
| Methyl Orange | Bright orange | Yellow | Yellow | Yellow | Yellow | Yellow |
| Merocyanine 540 | Hot pink | Light purple | Light purple | Light purple | Light purple | Light purple |
| Iron III Chloride Porphyrin* | Light mustard yellow | Darker mustard yellow | Darker mustard yellow | Darker mustard yellow | Darker mustard yellow | Darker mustard yellow |

*Dissolved in water

TABLE 6

Color Change Observations for Gram Negative Microorganisms

| Colorant | Initial Color | Color Change w/E. coli | Color Change w/P. aeruginosa | Color Change w/K. pneumoniae | Color Change w/P. mirabilis |
|---|---|---|---|---|---|
| Plasmocorinth B | Deep pink | Light purple | Deep blue | Deep reddish pink | Deep reddish pink |
| Nitro blue tetrazolium | Yellowish white | No change | No change | No change | No change |
| Alizarin Complexone | Yellow | Purple | Deeper purple | Brownish purple | Purple |

TABLE 6-continued

Color Change Observations for Gram Negative Microorganisms

| Colorant | Initial Color | Color Change w/E. coli | Color Change w/P. aeruginosa | Color Change w/K. pneumoniae | Color Change w/P. mirabilis |
|---|---|---|---|---|---|
| Orcein | Muddy purple | Light purple | Dark purple | Brownish purple | Darker brownish purple |
| Tetra Methyl-para-phenylene diamine (TMPD)* | Bright lavender | Colorless | Dark purple | Colorless | Colorless |
| Nile Red | Bright purple | Light pink | Light pink | Light pink | Light pink |
| Eriochrome Blue Black B | Dark Muddy purple | Bluish purple | Dark blue | Darker purple | Darker purple |
| Phenol Red | Yellow | Orange | Dark red/orange | Yellow with orange border | Orange |
| Alizarin Red S | Yellow | Brownish purple | Deep reddish purple | Light brownish purple | Deep reddish purple |
| Carminic Acid* | Reddish peach | Blueish purple | Dark purple | Paler Bluish purple | Purple |
| Fe(III)C$_3$ | White | No change | No change | Not tested | No change |
| Celestine Blue | Dark lavender | Blue | Blue | Blue | Blue |
| Kovac's Reagent | Pale yellow | White with greenish center and yellow border | White with greenish center and yellow border | White with greenish center and yellow border | White with greenish center and yellow border |
| Chrome Azurol S | Pink | Greenish yellow with dark pink border | Bright yellow with dark pink border | Greenish yellow with dark pink border | Greenish yellow with dark pink border |
| Universal Indicator 3–10 | Peach | Lighter peach with yellow center | Light green | Darker peach with yellow center | Lighter peach with yellow center |
| Methyl Orange | Bright orange | Yellow | Yellow | Yellow | Orange/yellow |
| Merocyanine 540 | Hot pink | Yellowish pink | Yellowish pink | Yellowish pink | Yellowish pink |
| Iron III Chloride Porphyrin* | Mustard yellow | Darker mustard yellow | Darker mustard yellow | Darker mustard yellow | Darker mustard yellow |

*Dissolved in water

With the exception of Methyl Orange, Nile Red, Tetra Methyl-para-phenylene diamine (TMPD), and Merocyanine 540, the observed color change was also most immediate (1 to 2 minutes).

Example 5

The ability to rapidly detect upper respiratory pathogens utilizing a group of colorants was demonstrated. The colorants tested were Alizarin Red S, Universal Indicator 3-10, Nile Red, Plasmocorinth B, Iron III Porphyrin, Eriochrome Blue Black B, Chrome Azurol S, Orcein, Alizarin Complexone, Phenol Red, Carminic Acid, Methyl Orange, and TMPD. The upper respiratory infection pathogens tested were *H. influenzae, M. lacunata, S. pyogenes, S. pneumoniae, A. pullulans*, and *P. janthinellum*. The colorant samples were prepared in a manner similar to Example 1. Unless otherwise specified, the colorants were dissolved in dimethylformamide (DMF). Color changes in the colorants were observed and recorded for each of the samples tested. Table 7 presents the observations from the upper respiratory infection pathogens.

TABLE 7

Color Change for Upper Respiratory Infection Pathogens

| Colorant | Initial Color | Color Change w/ H. influenzae | Color Change w/M. lacunata | Color Change w/ S. pyogenes | Color Change w/ S. pneumoniae | Color Change w/A. pullulans | Color change w/P. janthinellum |
|---|---|---|---|---|---|---|---|
| Alizarin Red S | Dark mustard yellow | Red | Brownish red | Light brown | Light brown | Bright brownish yellow | Bright brownish yellow |

TABLE 7-continued

Color Change for Upper Respiratory Infection Pathogens

| Colorant | Initial Color | Color Change w/ H. influenzae | Color Change w/M. lacunata | Color Change w/ S. pyogenes | Color Change w/ S. pneumoniae | Color Change w/A. pullulans | Color change w/P. janthinellum |
|---|---|---|---|---|---|---|---|
| Universal Indicator 3–10 | Dark peach | Greenish yellow | Greenish yellow | Brownish yellow | Brownish yellow | Darker peach | Darker peach |
| Nile Red | Bright purple | Pink | Pink | Pink | Pink | Dark pink | Dark pink |
| Plasmocorinth B | Bright pink | Bluish purple | Darker bluish purple | Dark pink | Dark pink | Lighter bright pink | Lighter bright pink |
| Iron III Porphyrin* | Mustard yellow | Darker mustard yellow | Darker mustard yellow | Darker mustard yellow | Darker mustard yellow | Darker mustard yellow | Darker mustard yellow |
| Eriochrome Blue Black B | Grape | Dark blue | Dark blue | Dark grapish pink | Dark grapish pink | Dark grape | Dark grape |
| Chrome Azurol S | Light orange | Light green with dark red border | Light green with dark red border | Brownish red with dark red border | Brownish red with dark red border | Light pink with dark red border | Light pink with dark red border |
| Orcein | Muddy purple | Bright purple | Bright purple | Bluish muddy purple | Darker muddy purple | Lighter muddy purple | Lighter muddy purple |
| Alizarin Complexone | Yellow | Reddish purple | Purple | Brown | Brown | Yellow | Yellow |
| Phenol Red | Orangish yellow | Orangish red | Bright red | Greenish yellow | Greenish yellow | Bright yellow | Bright yellow |
| Carminic Acid* | Bright peach | Purple | Dark purple | Brownish/purplish peach | Brownish/purplish peach | Brighter peach | Brighter peach |
| Methyl Orange | Dark orange | Yellow | Yellow | Yellow | Yellow | Browinsh yellow | Brownish yellow |
| TMPD* | Yellowish | White | Purple | Not tested | Pink | Not tested | Not tested |

*Dissolved in water

With the exception of Methyl Orange, Nile Red, and tetramethyl-para-phenylene diamine (TMPD), the observed color change was almost immediate (1 to 2 minutes).

Example 6

Filter paper (available from VWR International) was treated with solutions of Chrome Azurol, Alizarin Complexone, Plasmocorinth B, and Phenol Red (all dissolved in DMF). The samples were hung dry to evaporate the solvent. Solutions of C. albicans, E. coli, and S. aureus were diluted in ten-fold dilutions using Trypticase Soybean Broth (TSB) media, and is some cases, sterile water. Concentrations ranged from $10^8$ CFU/mL (stock solution) down to $10^1$ CFU/mL for both E. coli and S. aureus, and $10^7$ CFU/mL (stock solution) down to $10^1$ CFU/mL for C. albicans. TSB and water were used as control solutions. 100 µL aliquots of each solution were applied to the samples. The color changes are summarized in Tables 8-12.

TABLE 8

Response to Dilutions of C. albicans in TSB media

| Dye | Initial Color | $10^6$ CFU/ml | $10^5$ CFU/ml | $10^4$ CFU/ml | $10^3$ CFU/ml | $10^2$ CFU/ml | $10^1$ CFU/ml | TSB Control |
|---|---|---|---|---|---|---|---|---|
| Phenol Red | Bright yellow | orange | Slightly darker orange | Slightly darker orange | Slightly darker orange | Slightly darker orange | Slightly darker orange | Dark orange |
| Plasmocorinth B | Bright pink | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Brownish purple | Slightly darker Brownish purple | Slightly darker Brownish purple | Slightly darker Brownish purple | Slightly darker Brownish purple | Slightly darker Brownish purple | Dark Brownish purple |
| Chrome Azurol | rose | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 9

Response to Dilutions of S. aureus in TSB media

| Dye | Initial Color | 10⁸ CFU/ml (undiluted) | 10⁷ CFU/ml | 10⁶ CFU/ml | 10⁵ CFU/ml | 10⁴ CFU/ml | 10³ CFU/ml | 10² CFU/ml | TSB Control |
|---|---|---|---|---|---|---|---|---|---|
| Phenol Red | Bright yellow | Bright yellow | orange | Slightly darker orange | Slightly darker orange | Slightly darker orange | Slightly darker orange | Slightly darker orange | Dark orange |
| Plasmocorinth B | Bright pink | Bright purplish pink | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Light brown | Brownish purple | Slightly darker Brownish purple | Slightly darker Brownish purple | Slightly darker Brownish purple | Slightly darker Brownish purple | Slightly darker Brownish purple | dark Brownish purple |
| Chrome Azurol | rose | Brownish yellow | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 10

Response to Dilutions of S. aureus in water

| Dye | Initial Color | 10⁷ CFU/ml (in H₂O) | Water Control |
|---|---|---|---|
| Phenol Red | Bright yellow | N/A | Light yellow |
| Plasmocorinth B | Bright pink | Bright pink | Light pink |
| Alizarin Complexone | Bright yellow | Pale yellow | Pale yellow |
| Chrome Azurol | rose | Greenish red-pink | Light red-pink |

TABLE 11

Response to Dilutions of E. coli in TSB media

| Dye | Initial Color | 10⁸ CFU/ml (undiluted) | 10⁷ CFU/ml | 10⁶ CFU/ml | 10⁵ CFU/ml | 10⁴ CFU/ml | 10³ CFU/ml | 10² CFU/ml | TSB Control |
|---|---|---|---|---|---|---|---|---|---|
| Phenol Red | Bright yellow | Light orange | orange | Slightly darker orange | Slightly darker orange | Slightly darker orange | Slightly darker orange | Slightly darker orange | Dark orange |
| Plasmocorinth B | Bright pink | Pinkish purple | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Purplish brown | Brownish purple | Slightly darker Brownish purple | Slightly darker Brownish purple | Slightly darker Brownish purple | Slightly darker Brownish purple | Slightly darker Brownish purple | dark Brownish purple |
| Chrome Azurol | rose | Light green | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 12

Response to Dilutions of E. coli in water

| Dye | Initial Color | 10⁷ CFU/ml (in H₂O) | Water Control |
|---|---|---|---|
| Phenol Red | Bright yellow | Orangish yellow | Light yellow |
| Plasmocorinth B | Bright pink | Bright pink | Light pink |
| Alizarin Complexone | Bright yellow | Brownish yellow | Pale yellow |
| Chrome Azurol | rose | Dark green | Light red-pink |

Thus, a color change was observed for the microorganisms that was different than the media alone, although the difference was somewhat more subtle for the dilute solutions. Without intending to be limited in theory, it is believed that the more subtle difference for the dilute solutions was due in part to the lack of time given to the microorganisms to condition the media (the experiment was conducted shortly after dilution). In contrast, the stock solutions contained microorganisms that had been in the media for 24 hours.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting a microorganism in a sample, the method comprising:
   contacting the sample with an array, the array comprising a plurality of individual array addresses spaced apart in a predetermined pattern on a solid support, wherein the addresses each contain a colorant so that the array produces a visually observable spectral response;
   detecting the spectral response; and
   correlating the detected spectral response to the presence of one or more microorganisms.

2. The method of claim 1, wherein one or more of the addresses contain a pH-sensitive colorant.

3. The method of claim 2, wherein the pH sensitive colorant is a phthalein, hydroxyanthraquinone, arylmethane, aromatic azo, or a derivative thereof.

4. The method of claim 1, wherein one or more of the addresses contain a metal complexing colorant.

5. The method of claim 1, wherein one or more of the addresses contain a solvatochromoatic colorant.

6. The method of claim 1, wherein the array contains from 2 to 50 individual array addresses.

7. The method of claim 1, wherein the array contains from 3 to 40 individual array addresses.

8. The method of claim 1, wherein at least two of the addresses are spaced apart a distance of from about 0.01 to about 100 millimeters.

9. The method of claim 1, wherein at least two of the addresses are spaced apart a distance of from about 0.1 to about 50 millimeters.

10. The method of claim 1, wherein the spectral response is correlated to the presence of one or more microorganisms at a concentration of about $1\times10^3$ or more colony forming units per milliliter of the sample.

11. The method of claim 1, wherein the spectral response is correlated to the presence of one or more microorganisms at a concentration of about $1\times10^6$ or more colony forming units per milliliter of the sample.

12. The method of claim 1, wherein the colorant is applied to the solid support in the form of a composition that comprises a carrier.

13. The method of claim 12, wherein the colorant constitutes from about 0.1 to about 100 milligrams per milliliter of the carrier.

14. The method of claim 12, wherein the colorant constitutes from about 0.5 to about 60 milligrams per milliliter of the carrier.

15. The method of claim 1, wherein the array is printed onto the support.

16. The method of claim 1, wherein the spectral response is detected and compared to a control array.

17. The method of claim 1, wherein the spectral response is visually detected.

18. The method of claim 1, wherein the spectral response is produced in about 30 minutes or less after the array is contacted with the sample.

19. The method of claim 1, wherein the spectral response is produced in about 5 minutes or less after the array is contacted with the sample.

20. The method of claim 1, wherein the microorganism is a fungus.

21. The method of claim 20, wherein the fungus is *C. albicans, A. pullulans, P. janthinellum*, or a mixture thereof.

22. The method of claim 1, wherein the microorganism is a bacteria.

23. The method of claim 22, wherein the bacteria is a gram-positive bacteria.

24. The method of claim 23, wherein the gram-positive bacteria is *S. aureus, L. acidophilus, S. epidermidis, B. subtilis, E. faecalis, S. pyogenes, S. pneumoniae*, or a mixture thereof.

25. The method of claim 22, wherein the bacteria is a gram-negative bacteria.

26. The method of claim 25, wherein the gram-negative bacteria is *E. coli, P. aeruginosa, K. pneumoniae, P. mirabilis, M. lacunata, H. influenzae*, or a mixture thereof.

* * * * *